United States Patent [19]

Owen et al.

[11] Patent Number: 6,118,001
[45] Date of Patent: *Sep. 12, 2000

[54] HYDROXAMIC AND CARBOXYLIC ACID DERIVATIVES HAVING MMP AND TNF INHIBITORY ACTIVITY

[75] Inventors: David Alan Owen; John Gary Montana; John Fraser Keily; Robert John Watson; Andrew Douglas Baxter, all of Cambridge, United Kingdom

[73] Assignee: Darwin Discovery, Ltd., United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/908,397

[22] Filed: Aug. 7, 1997

[30] Foreign Application Priority Data

Aug. 7, 1996 [GB] United Kingdom ............ 9616599
Apr. 11, 1997 [GB] United Kingdom ............ 9707427

[51] Int. Cl.$^7$ ............ C07D 211/96; C07D 207/48; C07D 235/02; C07D 237/04
[52] U.S. Cl. ............ 546/229; 548/578; 548/300.1; 548/326.5; 548/335.5; 544/239; 544/235
[58] Field of Search ............ 548/578, 300.1, 548/326.5, 333.5; 546/229; 54/239, 235

[56] References Cited

U.S. PATENT DOCUMENTS 4,325,964 4/1982 Lafon ............ 424/282
5,698,706 12/1997 Baxter et al. ............ 548/314.7

FOREIGN PATENT DOCUMENTS

| 0780386 | 6/1997 | European Pat. Off. . |
| 9320047 | 10/1993 | WIPO . |
| 9523790 | 9/1995 | WIPO . |
| 9718188 | 5/1997 | WIPO . |
| 9724117 | 7/1997 | WIPO . |

OTHER PUBLICATIONS

Eckstein, Z., and J. Tolak (1963) "On the Properties and Fungicidal Activity of Aryloxyalkanehydroxamic Acids. VI. Influnces of Iodines as Subtituent" vol. XI, No. 12, pp. 671–675.

Zayed, S.M.A.D., et al. (1966) "Preparation and Fungicidal Properties of Some Arythioalkanoyl– and (Arylsulphonyl)–aceto–hydroxamic Acids" Zeitschrift Für Naturforschung, pp. 180–182.

Eckstein, Z., et al. (1958) "Hydroxamic Acids. VI. Chemical Properties and fungicidal actibity of some derivattives of Aryloxyacetohydroxamic Acids" Chemical Abstracts, vol. 52, No. 14, Column 11786, Abstract No. 11786h.

*Primary Examiner*—Johann Richter
*Assistant Examiner*—Dominic Keating
*Attorney, Agent, or Firm*—Saliwanchik, Lloyd & Saliwanchik

[57] ABSTRACT

Disclosed are hydroxamic and carboxylic acid derivatives which are useful inhibitors of matrix metalloproteinase and/or TNFα-mediated diseases, including degenerative diseases and certain cancers.

17 Claims, No Drawings

HYDROXAMIC AND CARBOXYLIC ACID DERIVATIVES HAVING MMP AND TNF INHIBITORY ACTIVITY

FIELD OF THE INVENTION

This invention relates to hydroxamic and carboxylic acid derivatives, and to their use in medicine.

BACKGROUND TO THE INVENTION

Metalloproteinases, including matrix metalloproteinase (MMP), (human fibroblast) collagenase, gelatinase and TNF convertase (TACE), and their modes of action, and also inhibitors thereof and their clinical effects, are described in WO-A-9611209, WO-A-9712902 and WO-A-9719075, the contents of which are incorporated herein by reference. MMP inhibitors may also be useful in the inhibition of other mammalian metalloproteinases such as the adamalysin family (or ADAMs) whose members include TNF convertase (TACE) and ADAM-10, which can cause the release of TNFα from cells, and others, which have been demonstrated to be expressed by human articular cartilage cells and also involved in the destruction of myelin basic protein, a phenomenon associated with multiple sclerosis.

Compounds which have the property of inhibiting the action of metalloproteinases involved in connective tissue breakdown, such as collagenase, stromelysin and gelatinase, have been shown to inhibit the release of TNF both in vitro and in vivo. See Gearing et al (1994), Nature 370:555–557; McGeehan et al (1994), Nature 370:558–561; GB-A-2268934; and WO-A-9320047. All of these reported inhibitors contain a hydroxamic acid zinc-binding group, as do the imidazole-substituted compounds disclosed in WO-A-9523790. Other compounds that inhibit MMP and/or TNF are described in WO-A-9513289, WO-A-9611209, WO-A-96035687, WO-A-96035711, WO-A-96035712 and WO-A-96035714.

WO-A-9718188 discloses MMP inhibitors of the formula $$Ph^1\text{-}Ph^2\text{—}X\text{—}(CH_2)_{0\text{-}6}(CZ)_{0\text{-}1}\text{—}(CHR^1)_{0\text{-}1}\text{—}CO\text{—}NHOH$$

wherein $Ph^1$ and $Ph^2$ are each optionally-substituted phenyl; X is absent, O, NH or S; Z is $—CONR^2R^3$; and $R^1$ is H, alkyl, alkenyl, OH, optionally-substituted phenylalkyl or phenyl-$SO_{0\text{-}2}$-alkyl, or alkyl-$COOR^1$.

EP-A-0780386 discloses compounds having MMP and TNF inhibitory activity, of the formula $$Y\text{—}CO\text{—}CR^1R^2\text{—}CR^3\text{—}S(O)_nR^5$$

wherein n is 0, 1 or 2; Y is OH or NHOH; $R^1$ is H or lower alkyl; $R^2$ is H, lower alkyl, heteroalkyl, aryl, aralkyl, arylheteroalkyl, cycloalkyl, heteroaryl, heteroaralkyl, heteroarylheteroalkyl, heterocyclo, heterocyclo-lower alkyl, heterocyclo-lower heteroaryl or $NR^6R^7$; $R^3$ is H, lower alkyl, cycloalkyl, cycloalkylalkyl, aryl, aralkyl, heteroaryl, heteroaralkyl, heteroalkyl or lower alkoxy, $R^4$ is H, lower alkyl, cycloalkyl or cycaloalkylalkyl; and $R^5$ is lower alkyl, cycloalkyl, cycloalkylalkyl, aryl, aralkyl, heteroaryl or heteroaralkyl.

Compounds of EP-A-0780386 first disclosed in U.S. application Ser. No. 8939, filed Dec. 20, 1995, are of the same formula, wherein $R^1$ is H; $R^2$ is H, lower alkyl, aralkyl, cycloalkyl, cycloalkylalkyl, heterocyclo or $NR^6R^7$; $R^3$ is H, lower alkyl, cycloalkyl, cycloalkylalkyl or aralkyl; $R^4$ is H or lower alkyl; and $R^5$ is lower alkyl, aryl, aralkyl, heteroaryl or heteroaralkyl.

U.S. Pat. No. 4,325,964 discloses certain benzhydryl sulphinyl hydroxamates, as having utility in neuopsychic ailments.

Zayed et al, Zeitschrift für Naturforschung (1966) 180–182, discloses 3-phenylsulphonylpropanoic acid N-hydroxyamide, as a fungicide.

SUMMARY OF THE INVENTION

The invention encompasses novel compounds of formula (I) which are useful inhibitors of matrix metalloproteinases and/or TNFα-mediated diseases, including degenerative diseases and certain cancers.

Novel compounds according to the invention are of the general type represented by formula (I):

$$B\text{—}X\text{—}(CH_2)_n\text{—}CHR^1\text{—}(CH_2)_m\text{—}COY \qquad (I)$$

wherein m and n are both independently 0 or 1, but are not both 0;

X is O, $NR^3$ or $S(O)_{0\text{-}2}$;

Y is $OR^2$ or NHOH;

$R^1$ is H or a group (optionally substituted with $R^9$) selected from $C_{1\text{-}6}$ alkyl, $C_{2\text{-}4}$ alkenyl, aryl, $C_{1\text{-}4}$ alkyl-aryl, heteroaryl, $C_{1\text{-}6}$ alkyl-heteroaryl, heterocycloalkyl, $C_{1\text{-}4}$ alkyl-heterocycloalkyl, cycloalkyl and $C_{1\text{-}6}$ alkyl-cycloalkyl;

$R^2$ is H or $C_{1\text{-}6}$ alkyl;

$R^3$ is H, $C_{1\text{-}6}$ alkyl, $COR^2$, $CON(R^2)_2$ where each $R^2$ is the same or different, $CO_2R^4$ or $SO_2R^4$, and $R^4$ is $C_{1\text{-}6}$ alkyl;

B is $C_{1\text{-}6}$ alkyl-aryl, $C_{1\text{-}6}$ alkyl, cycloalkyl, $C_{1\text{-}6}$ alkyl-cycloalkyl, cycloalkenyl, heterocycloalkenyl, $C_{1\text{-}6}$ alkyl-heteroaryl, heterocycloalkyl, $C_{1\text{-}6}$ alkyl-heterocycloalkyl, aryl or heteroaryl, any of which groups is optionally substituted by a substituent selected from $R^5$, $C_{1\text{-}6}$ alkyl-$R^5$, $C_{2\text{-}6}$ alkenyl-$R^5$, aryl (optionally substituted with $R^5$), aryl-$C_{1\text{-}6}$ alkyl-$R^5$, $C_{1\text{-}6}$ alkyl-aryl (optionally substituted with $R^5$), heteroaryl-$C_{1\text{-}6}$ alkyl-$R^5$, cycloalkyl (optionally substituted with $R^5$), benzofused cycloalkyl (optionally substituted with $R^5$), heterocycloalkyl (optionally substituted with $R^5$), benzofused heterocycloalkyl (optionally substituted with $R^5$), and the groups:

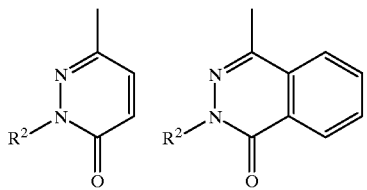

provided that B is not benzhydryl when X is SO and $R^1$ is H;

$R^5$ is $C_{1\text{-}6}$ alkyl, $C_{2\text{-}6}$ alkenyl-$R^7$, halogen, CN, $NO_2$, $NO_2$, $N(R^6)_2$, $OR^6$, $COR^6$, $CO_2R^2$, $CON(R^6)_2$, $NR^6R^7$, $S(O)_{0\text{-}2}R^3$ or $SO_2N(R^6)_2$;

$R^6$ is H or a group selected from $C_{1\text{-}6}$ alkyl, aryl, $C_{1\text{-}6}$ alkyl-aryl, heteroaryl, $C_{1\text{-}6}$ alkyl-heteroaryl, cycloalkyl, $C_{1\text{-}6}$ alkyl-cycloalkyl, heterocycloalkyl and $C_{1\text{-}6}$ alkyl-heterocycloalkyl, wherein said group is optionally substituted with $R^8$, $COR^8$, $SO_{0\text{-}2}R^8$, $CO_2R^8$, $OR^8$, $CONR^2R^8$, $NR^2R^8$, halogen, CN, $SO_2NR^2R^8$ or $NO_2$, and for each case of $N(R^6)_2$ the $R^6$ groups are the same or different or $N(R^6)_2$ is heterocycloalkyl optionally substituted with $R^8$, $COR^8$, $SO_{0\text{-}2}R^8$, $CO_2R^8$, $OR^8$, $CONR^2R^8$, $NR^2R^8$, halogen, CN, $SO_2NR^2R^8$ or $NO_2$;

$R^7$ is $COR^6$, $CON(R^6)_2$, $CO_2R^8$ or $SO_2R^8$;

$R^8$ is $C_{1\text{-}6}$ alkyl, aryl, $C_{1\text{-}6}$ alkyl-aryl, heteroaryl or $C_{1\text{-}6}$ alkyl-heteroaryl; and $R^9$ is $OR^6$, $COR^6$, $CO_2R^2$, $CON(R^6)_2$, $NR^6R^7$, $S(O)_{0-2}R^8$, $SO_2N(R^6)_2$, phthalimido, succinimido or the group

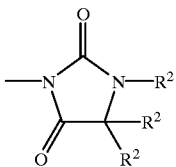

and the salts, solvates, hydrates, protected amino and protected carboxy derivatives thereof;

provided that the compound is not 3-phenylsulfonylpropanoic and N-hydroxy amide.

Combinations of substituents and/or variables are only permissible if such combinations result in stable compounds.

DESCRIPTION OF THE INVENTION

Preferred compounds of the invention are those wherein any one or more of the following apply:

X is S, SO or $SO_2$;

$R^1$ is H or a group (optionally substituted with $R^9$) selected from $C_{1-6}$ alkyl, $C_{2-6}$ alkenyl, $C_{1-6}$ alkyl-aryl, $C_{1-6}$ alkyl-heteroaryl, $C_{1-6}$ alkyl-heterocycloalkyl and $C_{1-6}$ alkyl-cycloalkyl;

B is $C_{1-6}$ alkyl-aryl, $C_{1-6}$ alkyl, cycloalkyl, cycloalkenyl, heterocycloalkenyl, $C_{1-6}$ alkyl-heteroaryl, aryl or heteroaryl, any of which groups is optionally substituted by a substituent selected from $R^5$, $C_{1-6}$ alkyl-$R^5$, aryl (optionally substituted with $R^5$), $C_{1-6}$ alkyl-heteroaryl (optionally substituted with $R^5$), heteroaryl (optionally substituted with $R^5$), heteroaryl-$C_{1-6}$ alkyl-$R^5$, heteroaryl-$C_{1-6}$ alkyl-$R^5$cycloalkyl (optionally substituted with $R^5$), benzofused cycloalkyl (optionally substituted with $R^5$), heterocycloalkyl (optionally substituted with $R^5$), benzofused heterocycloalkyl (optionally substituted with $R^5$), and the groups:

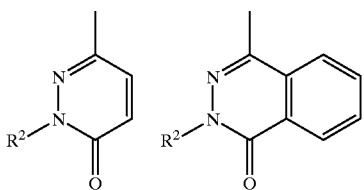

$R^5$ is halogen, CN, $NO_2$, $N(R^6)_2$, $OR^6$, $COR^6$, $CON(R^6)_2$, $NR^6R^7$, or $S(O)_{0-2}R^8$;

$R^7$ is $COR^6$; and $R^9$ is $OR^6$, $CO_2R^2$, $CON(R^6)_2$, phthalimido, succinimido or the group

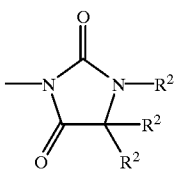

The compounds of the Examples are particularly preferred.

It will be appreciated that the compounds according to the invention can contain one or more asymmetrically substituted carbon atoms. The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

As used in this specification, alone or in combination, the term "$C_{1-6}$ alkyl" refers to straight or branched chain alkyl moiety having from one to six carbon atoms, including for example, methyl, ethyl, propyl, isopropyl, butyl, tert-butyl, pentyl, hexyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "cycloalkyl" refers to a saturated alicyclic moiety having from three to six carbon atoms and includes for example cyclopropyl, cyclobutyl, cyclopentyl, cyclohexyl and the like. "Benzofused cycloalkyl" includes indanyl and tetrahydronaphthyl.

The term "heterocycloalkyl" refers to a saturated heterocyclic moiety having from three to six carbon atoms and one or more heteroatom from the group N, O, S and includes for example azetidinyl, pyrrolidinyl, tetrahydrofuranyl, piperidinyl and the like. "Benzofused heterocycloalkyl" includes indolinyl and tetrahydroquinolinyl.

The term "cycloalkenyl" refers to an alicyclic moiety having from three to six carbon atoms and having in addition one double bond, This term would include for example cyclopentenyl or cyclohexenyl.

The term "heterocycloalkenyl" refers to an alicyclic moiety having from three to six carbon atoms and one or more heteroatoms from the group N, O, S and having in addition one double bond. This term includes, for example, dihydropyranyl.

The term "aryl" means an optionally substituted phenyl or naphthyl group with the substituent(s) being selected, for example, from halogen, trifluoromethyl, $C_{1-6}$ alkyl, alkoxy, phenyl and the like.

The term "heteroaryl" refers to aromatic ring systems of five to ten atoms of which at least one atom is selected from O, N and S, and includes for example furanyl, thiophenyl, pyridyl, indolyl, quinolyl and the like.

The term "alkoxy" refers to a straight chain or branched chain alkoxy group containing a maximum of six carbon atoms, such as methoxy, ethoxy, propoxy, isopropoxy, butoxy, tert-butoxy and the like.

The term "halogen" means fluorine, chlorine, bromine or iodine.

The terms "protected amino" and "protected carboxy" mean amino and carboxy groups which can be protected in a manner familiar to those skilled in the art. For example, an amino group can be protected by a benzyloxycarbonyl, tert-butoxycarbonyl, acetyl or like group, or may be in the form of a phthalimido or like group. A carboxyl group can be protected in the form of a readily-cleavable ester such as the methyl, ethyl, benzyl or tert-butyl ester.

Salts of compounds of formula (I) include pharmaceutically-acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically-labile ester of formula $CO_2R^{10}$ where $R^{10}$ may be an ethyl, benzyl, phenethyl, phenylpropyl, α- or β-naphthyl, 2,3-dimethylphenyl, 4-tert-butylphenyl, 2,2,2,-trifluoroethyl, 1-(benzyloxy)benzyl, 1-(benzyloxy)ethyl, 2-methyl-1-propionyloxypropyl, 2,4,6-trimethylbenzyloxymethyl or pivaloylmethyl group.

Compounds of the general formula (I) may be prepared by any suitable method known in the art and/or by the following processes.

It will be appreciated that, where a particular stereoisomer of formula (I) is required, the synthetic processes described herein may be used with the appropriate homochiral starting material and/or isomers maybe resolved from mixtures using conventional separation techniques (e.g. HPLC).

The compounds according to the invention may be prepared by the following process. In the description and formulae below the groups $R^1$, $R^2$, $R^3$, $R^4$, $R^5$, $R^6$, $R^7$, $R^8$, $R^9$, $R^{10}$, B, X and Y are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see Greene et al, "Protective Groups in Organic Synthesis", Wiley Interscience.

A process for preparing compounds of general formula (I) comprises alkylating a compound of formula B—XH (II) wherein B and X are as previously defined, with an alkylating agent of formula $Z-(CH_2)_n$—$CHR^1$—$(CH_2)_m$—COY (III) or (when m=0) an acrylate of formula $CH_2$=$CR^1$—COY (IV) wherein $R^1$ and Y are as defined previously and Z represents a suitable leaving group (e.g. a halogen such as bromine, or an alkylsulphonate ester such as methanesulphonate).

Alkylating agents (III) can be obtained in chiral or racemic form. Many of these derivatives can be readily obtained from commercially available starting materials using methods known to those skilled in the art (see WO-A-9005719).

Acrylates of formula (IV) may be prepared by the Mannich reaction (i.e. with paraformaldehyde and piperidine in a suitable organic solvent, such as 1,4-dioxane) on a dicarboxylic acid of general formula $HO_2C$—$CHR^1$—$CO_2H$ (V). This reaction involves an eliminative decarboxylation step resulting in the formation of an α, β-unsaturated carboxylic acid (i.e. where Y=OH) directly. This carboxylic acid can then be elaborated using standard chemistry, known to those skilled in the art, to provide esters (Y=$OR^2$) or hydroxamides (NHOR$^{11}$) where $R^{11}$ is a suitable protecting group such as benzyl, tert-butyl or tert-butyldimethylsilyl (TBDMS).

Dicarboxylic acids of formula (V) may be prepared by the alkylation of, for instance, diethyl malonate with an alkylating agent of formula $R^1$-Z (VI), wherein Z is as defined above, followed by hydrolysis under basic conditions.

Compounds of formula (II) in which B includes an aryl, heteroaryl, functional or other group as a substituent on a core part thereof (B'), may be prepared by palladium-catalysed coupling of an aryl, heteroaryl, functionalising or other compound with a compound of general formula A-B'-$XR^{12}$ (VII) wherein $R^{12}$ is a suitable protecting group such as a methyl, tert-butyl, benzyl or trityl, and A is a halide such as iodide, bromide or, in some instances, chloride. This is followed by removal of any protecting groups.

Many such palladium-catalysed coupling reactions are known to those skilled in the art and can provide compounds of formula (II) bearing substituents described by $R^5$ such as $COR^6$, $CO_2R^2$ or $CON(R^6)_2$, as well as aryl, heteroaryl, alkenyl or alkyl groups optionally substituted by $R^5$. Other groups described by B and/or $R^5$ can be introduced by standard chemical transformations known to those skilled in the art.

Many compounds of general formulae (II), (VI) and (VII) are commercially available or may be prepared, by standard aromatic, heteroaromatic or other chemistry known to those skilled in the art, from commercially-available materials.

If required, intermediates of general formulae (VIII) and (IX)

(VIII)

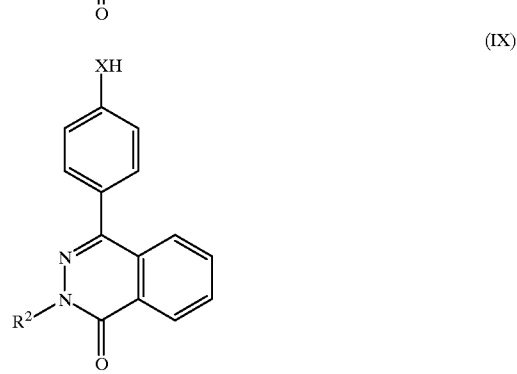

(IX)

may be prepared by Friedel-Crafts acylation of a simple aromatic system Ph-XH (X) with phthalic or maleic anhydride, followed by treatment with a hydrazine of general formula $H_2N$—$NHR^2$ (XI).

Compounds of formula (I) may also be prepared by interconversion of other compounds of formula (I). Thus, for example, a compound of formula (I) wherein $R^1$ is a $C_{1-6}$ alkyl group may be prepared by hydrogenation (using palladium on carbon in suitable solvent, such as an alcohol, e.g. ethanol) of a compound of formula (I) wherein $R^1$ is a $C_{2-6}$ alkenyl group. Further, a compound of formula (I) wherein X is $S(O)_{1-2}$ may be prepared by oxidation of a compound of formula (I) wherein X is S.

Carboxylic acids of general formula (I) (Y=OH), may be converted to other compounds of formula (I) such as esters (Y=$OR^2$) or hydroxamic acids (Y=NHOH) using methods known to those skilled in the art.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to the stromelysins, collagenases and gelatinases. Compounds according to the invention also exhibit in vitro inhibition of TNF release, TNF receptor shedding, IL-6 receptor shedding and L-selection shedding.

The 80 kD TNF receptor ($TNFR_{80}$) is proteolytically cleaved at the cell surface (shed), releasing a soluble ligand-binding receptor fragment. Interestingly, the processing of $TNF\alpha$ and shedding of $TNFR_{80}$ have been demonstrated to occur concurrently in activated T-cells, arousing speculation that a common protease may be involved. It has been shown by Crowe et al, J. Exp. Med., (1995) 181:1205, that a synthetic inhibitor of TNF processing also blocks the shedding of $TNFR_{80}$, suggesting that these processes may be coordinately regulated during T-cell activation. Notably, the protease cleavage site in pro-TNF(Ala-Val) is also present in the extracelular domain of $TNFR_{80}$ ($Ala^{213}$-$Val^{214}$) at a site consistent with the observed molecular weight of the shed receptor fragment. Thus, metalloproteinase inhibitors may offer protection from the deleterious systemic effects of $TNF\alpha$ at two levels simultaneously, firstly by preventing the release of soluble $TNF\alpha$, and secondly by blocking the accumulation of shed $TNFR_{80}$.

Synergistically with TNF, metalloproteinase inhibitors also inhibit the release of APO-1/Fas (CD95) ligand (APO-1L) which induces apoptosis in sensitive target cells. The shedding APO-1/Fas (CD95), a type I transmembrane glycoprotein belonging to the nerve growth factor/TNF receptor sub-family is also blocked by known metalloproteinase inhibitors but not by common inhibitors of serine/cysteine proteases; see Mariani et al, Eur. J. Immunol., (1995) 25:2303. Several other important receptors expressed by activated T- and B-cells have also been demonstrated to be shed from the cell surface by the action of metalloproteinases. These enzymes, collectively known as sheddases, provide new targets for inhibitors of metalloproteinases, including compounds of the present invention.

The activity and selectivity of the compounds may be determined by use of the appropriate enzyme inhibition test, for example as described in Examples A–M, below. Certain compounds of this invention have selective inhibitory activity, in particular inhibition of MMP substantially without inhibition of TNF release and related activities as defined above. This may be of particular value where such activities are associated with reduced side-effects.

This invention also relates to a method of treatment for patients (including man and/or mammalian animals raised in the dairy, meat or fur industries or as pets) suffering from disorders or diseases which can be attributed to stromelysin as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns:

a method of management (by which is meant treatment of prophylaxis) of disease or conditions mediated by TNF and/or MMPs in mammals, in particular in humans, which method comprises administering to the mammal an effective amount of a compound of formula (I) above, or a pharmaceutically acceptable salt thereof; and a compound of formula (I) for use in human or veterinary medicine, particularly in the management (by which is meant treatment or prophylaxis) of diseases or conditions mediated by TNF and/or MMPs; and the use of a compound of formula (I) in the preparation of an agent for the management (by which is meant treatment or prophylaxis) of diseases or conditions mediated by TNF and/or MMPs.

The disease or conditions referred to above include inflammatory diseases, autoimmune diseases cancer, cardiovascular diseases, diseases involving tissue breakdown such as rheumatoid arthritis, osteoarthritis, osteoporosis, neurodegeneration, Alzheimer's disease, stroke, vasculitis, Crohn's disease, ulcerative colitis, multiple sclerosis, periodontitis, gingivitis and those involving tissue breakdown such as bone resorption, haemorrhage, coagulation, acute phase response, cachexia and anorexia, acute infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, opthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis and endosclerosis.

For the treatment of rheumatoid arthritis, osteoarthritis, and in diseases and indications resulting from the over-expression of matrix metalloendoproteinases such as found in certain metastatic tumour cell lines or other diseases mediated by the matrix metalloendoproteinases or increased TNF production, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874, to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylele sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. For the purposes of this specification, topical application includes mouth washes and gargles.

Dosage levels of the order of from about 0.05 mg to about 140 mg per kilogram of body weight per day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples illustrate the invention.

In the Examples, the following abbreviations are used:

| | |
|---|---|
| TNFα | Tumour Necrosis Factor α |
| LPS | Lipopolysaccharide |
| ELISA | Enzyme linked immunosorbant assay |
| EDC | 1-Ethyl-2-dimethylaminopropylcarbodiimide |
| RT | Room Temperature |

Intermediate 1

4-Acetylthiophenol

Was prepared according to EP 302321.

TLC $R_f$ 0.3 (5% methanol-dichloromethane)

Intermediate 2

Bis(4-Benzenecarboxylate)disulfide

Iodine (1.23 g) was added portionwise to a solution of 4-mercaptobenzoic acid (1.5 g) in methanol (30 ml) at room temperature. Stirring was continued for three hours. Water (1 ml) and sodium sulfite (0.2 g) were added, and the reaction was stirred for 30 minutes. Methanol was removed in vacuo and the title compound was isolated by filtration as a white solid (1.38 g, 93%).

TLC $R_f$ 0.05 (2.5% methanol-dichloromethane)

Intermediate 3

Bis(4-N,N-Dimethylcarboxamidebenzene)disulfide

A solution of intermediate 2 (0.5 g) in a mixture of tetrahydrofuran (15 ml) and DMF (7 ml) was stirred at room temperature. Dimethylamine hydrochloride (0.27 g), triethylamine (1.37 ml) and EDAC (0.63 g) were added and the reaction was stirred overnight. Solvents were removed in vacuo and the residue partitioned between water and ethyl acetate. The aqueous phase was extracted with ethyl acetate and the combined organics were dried over $MgSO_4$, filtered, and concentrated in vacuo to give the crude product, which was purified by column chromatography on silica eluting with 5% methanol in dichloromethane. The title compound was isolated as a white solid (0.245 g, 42%).

TLC $R_f$ 0.24 (5% methanol-dichloromethane)

Intermediate 4

4-Sulfanyl-N,N-dimethylbenzamide

Sodium borohydride (0.076 g) was added portionwise to a solution of intermediate 3 (0.245 g) in ethanol (10 ml) at room temperature, and the mixture was stirred for 16 h. The solvent was then removed in vacuo and the residue was taken up in water. The resulting solution was acidified to pH 2, then extracted with ethyl acetate. Removal of the solvents gave the title compound as a white solid (0.23 g, 93%).

TLC $R_f$ 0.41 (5% methanol-dichloromethane)

Intermediate 5

1-Bromo-5-phenylpentan-2-one

Diazomethane preparation: The reaction vessel of a standard diazomethane kit (fitted with a $CO_2$ condenser and trap and an addition funnel) was charged with a solution of potassium hydroxide (5.00 g) in water (8 ml) and ethanol (10 ml). The vessel was heated to 65° C. and a solution of N-methyl-N-nitroso-4-toluene sulfonamide (Diazald,® 5.00 g) in diethyl ether (45 ml) was added dropwise over 30 min from an addition funnel. Diazomethane solution was collected by continuous distillation. Ethyl chloroformate was added dropwise to a stirred solution of 4-phenylbutyric acid (1.36 g) and N-methylmorpholine (1.28 ml) in THF (15 ml) at −12° C. under a nitrogen atmosphere. A white precipitate began to form, which was removed by filtration after 90 min. The filtrate was treated with a pre-formed solution of diazomethane (16.6 mmol) in diethyl ether at 0° C. The combined solution of diazomethane and anhydride was stirred at 0° C. for 3.5 h and room temperature for 1 h. A solution of hydrogen bromide in acetic acid (45%, 10 ml) and water (10 ml) was added slowly. The mixture was stirred for 20 min before a saturated aqueous solution of $NaHCO_3$ (200 ml) was added. The mixture was extracted with ethyl acetate (3×200 ml) and the combined extracts were washed with brine and dried ($MgSO_4$). The solvent was removed in vacuo and the residue was eluted from a column of silica with 10% diethyl ether in hexane to provide the title compound as a colourless liquid (765 mg, 38%).

TLC $R_f$ 0.6 (3:1 hexane-diethyl ether).

Intermediate 6

1-(4-Methoxyphenylsulfanyl)-5-phenylpentan-2-one

A solution of intermediate 5 (365 mg) and 4-methoxythiophenol (0.186 ml) in DMF (15 ml) at room temperature under a nitrogen atmosphere was treated with triethylamine (0.210 ml). The mixture was stirred for 4 h before being poured into 0.5 N HCl (100 ml). The mixture was extracted with ethyl acetate (3×100 ml) and the combined extracts were washed with brine and dried ($MgSO_4$). The solvent was removed in vacuo and the residue was eluted from a column of silica with 10% diethyl ether in hexane to provide the title compound as a colourless solid (375 mg, 83%).

TLC $R_f$ 0.3 (3:1 hexane-diethyl ether).

Intermediate 7

Methyl 3-(4-Methoxyphenylsulfanyl)methyl-6-phenylhex-2-enoate

Methyl diethyl phosphonoacetate (0.246 ml) was added dropwise to a stirred solution of potassium hexamethyldisilazide (0.5 M in toluene, 2.67 ml) in THF (20 ml) at −12° C. under a nitrogen atmosphere. The mixture was stirred for 20 min before a solution of intermediate 6 (365 mg) in THF (20 ml) at −12° C. was added via a double-tipped needle under pressure of nitrogen. The mixture was stirred at a temperature not exceeding 0° C. for 1 h before being allowed to warm to room temperature and then heated to 40° C. for a period of 20 h. A saturated aqueous solution of $NH_4Cl$ (100 ml) was added. The mixture was extracted with ethyl acetate (3×100 ml) and the combined extracts were washed with brine and dried ($MgSO_4$). The solvent was removed in vacuo and the residue was eluted from a column of silica with 10% diethyl ether in hexane to provide the title compound as an equal mixture of E and Z isomers as a colourless liquid (265 mg, 61%).

TLC $R_f$ 0.25 and 0.35 (5:1 hexane-diethyl ether).

Intermediate 8

Methyl-3-(4-Methoxyphenylsulfanyl)methyl-6-phenyl-hexanoate

A solution of intermediate 7 (265 mg) in ethyl acetate (20 ml) was added to an evacuated hydrogenation flask containing 10% palladium on charcoal (150 mg). The mixture was degassed before being flushed with hydrogen and agitated overnight. The catalyst was then removed by filtration over Celite® and the solvent was removed in vacuo to give the title compound as a pale yellow liquid (242 mg, 91%).

TLC $R_f$ 0.4 (5:1 hexane-diethyl ether)

Intermediate 9

Bis(4-Hydroxybenzene)disulfide

Iodine (5.12 g) was added portionwise to a stirred solution of 4-hydroxythiophenol (5.09 g) in methanol (50 ml) at ambient temperature. After stirring for 2 hours, water (2 ml)

Intermediate 10

Bis(4-Carbamoylmethyloxybenzene)disulfide

Intermediate 9(3.00 g), 2-bromoacetamide (3.47 g) and potassium carbonate (3.48 g) were heated in acetone (100 ml) at reflux. After 7 hours the mixture was cooled in ice, and a white solid which precipitated was removed by filtration, washed with acetone, water and acetone and dried to constant weight in vacuo to provide the title compound (3.659 g, 84%) as a colourless solid.

TLC $R_f$ 0.23 (5% methanol-dichloromethane)

Intermediate 11

2-(4-Sulfanylphenoxy)acetamide

Intermediate 10 (1.46 g) and sodium borohydride (0.45 g) were heated to reflux in absolute ethanol for 90 minutes. Sodium borohydride was added to the refluxing mixture (CAUTION) until the reaction was complete by thin layer chromatography. After cooling, the solution was concentrated to dryness in vacuo, and the residue suspended in water (40 ml). The basic aqueous mixture was acidified with concentrated hydrochloric acid and extracted with diethyl ether (100 ml). The ethereal solution was washed with water (2×50 ml), saturated brine (20 ml), dried (MgSO$_4$) and concentrated to dryness in vacuo to provide the title compound (1.22 g, 84%) as an orange solid.

TLC $R_f$ 0.54 (5% methanol-dichloromethane)

Intermediate 12

Dibenzyl(3-Succinimidopropyl)malonate

Sodium hydride (60% dispersion in mineral oil, 4.4 g) was added to a solution of dibenzyl malonate (29.5 g) in THF (300 ml) and the mixture was stirred at room temperature for 30 min, then a solution of 1-bromo-3-chloropropane (10 ml) in THF (30 ml) was added dropwise. The solution was heated at reflux for 18 h, then cooled and evaporated in vacuo. The oily residue was dissolved in hexane (500 ml) and washed with water and brine, then dried (MgSO$_4$) and evaporated to give a colourless oil. This oil was dissolved in acetone (300 ml) and sodium iodide (20 g) was added. The solution was stirred at room temperature for 18 h, then evaporated and the residue partitioned between water and hexane. The layers were separated and the organic layer was dried (MgSO$_4$) and evaporated to give a pale yellow oil which was dissolved in dry DMF. Potassium succinimide (15 g) was added and the mixture was heated at 80° C. for 18 h. The mixture was cooled, poured into water (500 ml) and extracted with diethyl ether (3×200 ml). The ether layers were combined, washed with water, dried and evaporated. The residue was purified by column chromatography, eluting with diethyl ether, to give the title compound (9.65 g, 23%) as a colourless oil.

TLC $R_f$ 0.45 (diethyl ether)

Intermediate 13

1-(2-Bromoethyl)-3,4,4-trimethylhydantoin

Sodium hydride (60% dispersion in mineral oil, 1.7 g) was added to a solution of 3,4,4-trimethylhydantoin (5.5 g) in DMF (20 ml) at room temperature. The mixture was stirred for 30 min, then dibromoethane (3.5 ml) was added dropwise and the solution was stirred overnight. The mixture was added to water (200 ml) and extracted with diethyl ether. The ether layer was washed with water, dried (MgSO$_4$) and evaporated and the residue was purified by column chromatography, eluting with diethyl ether, to give the title compound (4.2 g, 50%) as a colourless solid.

TLC $R_f$ 0.5 (diethyl ether).

Intermediate 14

1-(3-Iodopropyl)-3,4,4-trimethylhydantoin

Sodium hydride (2.2 g) was added to a solution of 3,4,4-trimethylhydantoin (7.1 g) in DMF (50 ml) at room temperature and the mixture was stirred for 1 h. 3-Chloro-1-bromopropane (4.9 ml) was then added and the solution was stirred overnight. The mixture was then poured into water (300 ml) and extracted with diethyl ether; the ether layer was dried (MgSO$_4$) and evaporated and the residue was dissolved in acetone (100 ml) to which was added sodium iodide (10 g). The mixture was heated at reflux for 18 h, then evaporated and the residue was dissolved in diethyl ether and washed with water, then dried (MgSO$_4$) and evaporated to give the title compound (11 g, 70%) as a brown oil.

TLC $R_f$ 0.85 (diethyl ether)

Intermediate 15

4-Benzoylbenzenethiol

A stirred solution of sodium hydrosulfide monohydrate (43 g) in N-methylpyrrolidinone (400 ml) under a nitrogen atmosphere was heated at 160° C. under Dean and Stark conditions; 10 ml of water azeotrope was collected over 90 min. The mixture was cooled to 140° C. and 4-chlorobenzophenone (50 g) was added. The mixture was stirred at 160° C. for 3 h before being allowed to cool to room temperature overnight. The N-methylpyrrolidinone was removed in vacuo and the black oily residue was dissolved in water (500 ml). The solution was acidified with 6 N HCl and the mixture was extracted with ethyl acetate (3×300 ml). The combined extracts were washed with brine and the solvent was removed in vacuo to give a brown solid (41 g). The solid was dissolved in ethyl acetate (500 ml) and the solution was extracted with NaOH (5%, 4×200 ml). The combined extracts were acidified to pH 3 with 6 N HCl and the resulting precipitate was collected by filtration, washed with water and dried in vacuo to give the title compound as a beige solid (21 g, 43%).

TLC $R_f$ 0.4 (3:1 hexane-ethyl acetate)

Intermediate 16

Benzo[1,3]dioxole-5-thiol

Was prepared according to Hitotsuyangi et al (*J. Chem. Soc., Perkin Trans. 1*, 1995, 1387–1390) from 5-bromobenzo[1,3]dioxole, as a colourless oil (7.48 g, 61%).

TLC $R_f$ 0.5 (10% ethyl acetate/hexane)

--- and sodium sulfite (0.62 g) were added to decolourise the solution, and after brief stirring the mixture was concentrated to dryness in vacuo. The residual orange solid was partitioned between diethyl ether (50 ml) and water, and the layers were separated. The organic layer washed with water (3×20 ml), saturated brine (10 ml), dried (MgSO$_4$) and concentrated to dryness in vacuo to provide the title compound as a yellow solid (5.06 g, 100%).

TLC $R_f$ 0.29 (5% methanol-dichloromethane)

Intermediate 17

4-Acetylsulfanyltetrahydropyran

Diethyl azodicarboxylate (7.24 ml) was added to a stirred solution of triphenylphosphine (12.1 g) in THF (80 ml), and stirred at room temperature for 10 min. Thiolacetic acid (3.29 ml) and tetrahydro-4H-pyran-4-ol (2.3 g) were added (CAUTION: exotherm), and the mixture stirred at room temperature for a further 18 h. After removal of the THF under reduced pressure, stirring with hexane (50 ml) and water (50 ml) gave a precipitate, which was removed by filtration. The biphasic filtrate was separated, and the aqueous phase extracted once with hexane (50 ml). The combined hexane extracts were washed with water (30 ml), brine (10 ml), dried ($MgSO_4$) and evaporated to leave a yellow liquid (2.73 g). Purification by chromatography on silica, eluting with hexane/diethyl ether (10:1), provided the title compound as a pale yellow liquid (0.98 g, 27%).

TLC $R_f$ 0.20 (hexane/diethyl ether (10:1))

Intermediate 18

Tetrahydropyran-4-thiol

Sodium borohydride (0.278 g) was added to a stirred solution of intermediate 17 in methanol (15 ml) at 0° C. under nitrogen. After 2 h a further portion of sodium borohydride (0.370 g) was added, and the mixture allowed to warm to room temperature and stirred for a further 18 h. The reaction was then quenched with 1 M hydrochloric acid (50 ml) and extracted with diethyl ether (2×30 ml). The combined organic extracts were washed with brine (10 ml), dried ($MgSO_4$) and concentrated in vacuo to provide the title compound as a colourless liquid (0.472 g, 60%).

TLC $R_f$ 0.70 (hexane/ethyl acetate (3:1))

Intermediate 19

1-Benzoyl-4-bromopiperidine

Benzoyl chloride (1.41 g) was added to a solution of 4-bromopiperidine hydrobromide (2.45 g) in THF (30 ml) at 0° C., followed by triethylamine (2.2 g, 2.2 eq). The solution was stirred at room temperature for 1 h, and evaporated and. The residue was dissolved in dichloromethane (100 ml), washed with water, 1M HCl and saturated sodium bicarbonate, dried and evaporated to give the title compound as colourless oil (2.76 g, 100%).

TLC $R_f$ 0.55 (ether).

Intermediate 20

1-Benzoyl-4-(acetylsulfanyl)piperidine

Potassium thioacetate (2.3 g) was added to a solution of intermediate 19 in DMF (50 ml) at room temperature. The mixture was stirred at room temperature for 3 days, then added to water and extracted with ether. The solvent was washed with water and sodium bicarbonate solution, dried and evaporated to give the title compound as pale amber oil (2.6 g, 100%).

TLC $R_f$ 0.45 (ether).

Intermediate 21

1-Benzoylpiperidine-4-thiol

A solution of the thioacetate intermediate 20 (2.6 g) in methanol (100 ml) was treated with sodium borohydride (1.2 g) and the mixture was stirred at room temperature for 4 h, then evaporated and the residue dissolved in water. The solution was acidified with solid citric acid and extracted with dichloromethane (2×100 ml). The solvent was washed with brine, dried and evaporated to give the title compound as brown oil (2.0 g).

TLC $R_f$ 0.30 (ether).

Intermediate 22

1-tert-Butyloxycarbonyl-4-bromopiperidine

A solution of di-tert-butyldicarbonate (4.4 g) in dichloromethane was added to a suspension of 4-bromopiperidine hydrobromide (5 g) in dichloromethane (100 ml) at 0° C., followed by triethylamine (5.1 g). The solution was stirred for 3 h at room temperature, then washed with water, 0.5 M HCl and saturated sodium bicarbonate, dried and evaporated to give the title compound as colourless oil (5.3 g, 99%).

TLC $R_f$ 0.70 (ether).

Intermediate 23

1-tert-Butyloxycarbonyl-4-(acetylsulfanyl)piperidine

Potassium thioacetate (4.4 g) was added to a solution of intermediate 22 (5.3 g) in DMF (100 ml) and the mixture was heated to 100° C. for 4 h, then cooled and added to water. The mixture was extracted with ether, and the solvent then washed with water and sodium bicarbonate, dried and evaporated to give the title compound (5.10 g, 96%).

TLC $R_f$ 0.60 (ether).

Intermediate 24

4-(4-Sulfanylbenzoyl)pyridine

A suspension of sodium hydrogen sulfide (6 g) in DMF (100 ml) was heated to reflux for 1 h, then cooled and 4-(4-chlorobenzoyl)pyridine (5 g) was added. The mixture was heated at reflux for 2 h, then cooled and added to water. The brown solution was washed with ether, then acidified with citric acid and extracted with dichloromethane (2×100 ml). The solvent was dried and evaporated to give the title compound as beige powder (2.4 g, 50%).

TLC $R_f$ 0.45 (ether).

Similarly prepared was:

Intermediate 25

2-(4-Sulfanylbenzoyl)thiophene

From 2-(4-fluorobenzoyl)thiophene (10 g) as beige solid (4.50 g, 42%).

TLC $R_f$ 0.65 (ether).

Intermediate 26

4-Methoxy-1-(2-Phenylethylsulfanyl)benzene

A solution of 4-methoxybenzene thiol (5.7 g), triethylamine (4.1 g) and 2-bromoethylbenzene (5.6 ml) in DMF (50 ml) at 0° C. was stirred for 2 h, then added to water and extracted with ether. The solvent was washed with water, 1M NaOH and brine, then dried and evaporated to give the title compound as colourless oil (8.9 g, 95%).

TLC $R_f$ 0.80 (ether)

Intermediate 27

Dibenzyl-2-(3-phthalimidopropyl)malonate

A solution of dibenzyl malonate (20 g) in anhydrous THF (200 ml) was treated at 0° C. with sodium hydride (60% dispersion in mineral oil, 3.1 g). The mixture was allowed to warm to room temperature and stirred for 30 minutes under nitrogen. The mixture was then treated with a solution of N-(3-bromopropyl)phthalimide (20.5 g) in THF (100 ml) and heated at reflux for 12 hours. The reaction was then cooled, filtered, and the filtrate evaporated in vacuo. The residue was partitioned between ethyl acetate (200 ml) and saturated aqueous ammonium chloride (150 ml). The organic layer was washed with water (100 ml), brine (100 ml), dried (MgSO$_4$), filtered and the filtrate evaporated in vacuo. The residue was purified by column chromatography on silica gel eluting with 20% ethyl acetate in hexane to yield the title compound (17.5 g, 50%) as a white solid.

TLC R$_f$ 0.16 (20% ethyl acetate-hexane)

Similarly prepared were:

Intermediate 28

Dibenzyl 2-(2-Phthalimidoethyl)malonate

From dibenzyl malonate (20 g) and N-(2-bromoethyl) phthalimide (18.7 g), as a clear gum (32 g, 100%).

TLC R$_f$ 0.15 (20% ethyl acetate-hexane)

Intermediate 29

Dibenzyl (2-(3,4,4-Trimethylhydantoin-1-yl)ethyl) malonate

From dibenzy malonate (4.8 g) and intermediate 13 (4.2 g), as a colourless oil (7.2 g, 100%).

TLC R$_f$ 0.4 (diethyl ether)

Intermediate 30

Dibenzyl(3-(3,4,4-Trimethylhydantoin-1-yl)propyl) malonate

From dibenzyl malonate (5.7 g) and intermediate 14 (6.2 g) as a colourless oil (7.1 g, 80%).

TLC R$_f$ 0.53 (diethyl ether)

Intermediate 31

Dibenzyl(3-Phenylpropyl)malonate

From dibenzyl malonate (30 g) and 1-bromo-3-phenylpropane (21 g) as a colourless oil (34 g, 80%).

TLC R$_f$ 0.48 (20% ethyl acetate-hexane)

Intermediate 32

Dibenzyl Propylmalonate

From dibenzyl malonate (22 ml) and 1-bromopropane (7.3 g) as a colourless oil (25.9 g, 100%).

TLC R$_f$ 0.31 (20% ethyl acetate—hexane)

Intermediate 33

Diethyl (3-(Ethoxycarbonyl)propyl)malonate

From diethyl malonate (5.0 g) and ethyl 4-bromobutyrate (6.65 g), as a clear gum (3.79 g, 45%).

TLC R$_f$ 0.29 (20% ethyl acetate in hexane)

Intermediate 34

2-Methylene-5-phthalimidopentanoic Acid

A solution of intermediate 27 (16.75 g) in dioxane (200 ml) was treated with 10% palladium on charcoal (1.7 g) and hydrogenated at atmospheric pressure until the hydrogen uptake had ceased. The catalyst was removed by filtration through Celite® and the filtrate treated with piperidine (3.2 g) at room temperature. After 30 minutes the reaction was treated with formaldehyde (37% solution in water, 15 ml), stirred for two hours at room temperature and then heated at 80° C. for two hours. The mixture was cooled, the solvent removed in vacuo and the residue partitioned between ethyl acetate (200 ml) and 10% aqueous citric acid (100 ml). The organic layer was washed with water (100 ml), brine (100 ml), dried over magnesium sulfate, filtered and the filtrate evaporated in vacuo. The residue was purified by column chromatography on silica gel eluting with 40% ethyl acetate in hexane to yield the title compound (12.2 g, 70%) as a white solid.

TLC R$_f$ 0.44 (50% ethyl acetate-hexane)

Similarly prepared were:

Intermediate 35

2-Methylene-4-phthalimidobutanoic Acid

From intermediate 28 (10 g) as a white solid (5 g, 93%).

TLC R$_f$ 0.12 (50% ethyl acetate-hexane)

Intermediate 36

2-Methylene-5-succinimidopentanoic Acid

From intermediate 12 (9.65 g) as colourless oil (2.85 g, 59%).

TLC R$_f$ 0.6 (diethyl ether).

Intermediate 37

2-Methylene-4-(3,4,4-trimethylhydantoin-1-yl) butananoic Acid

From intermediate 29 (7.2 g) as a colourless solid (1.5 g, 37%).

TLC R$_f$ 0.35 (ethyl acetate)

Intermediate 38

2-Methylene-5-phenylpentanoic Acid

From intermediate 31 (17.6 g) as a colourless oil (5.0 g, 60%).

TLC R$_f$ 0.31 (20% ethyl acetate-hexane)

Intermediate 39

2-Methylene-5-(3,4,4-trimethylhydantoin-1-yl) pentanoic Acid

From intermediate 30 (10 g) as a colourless oil (5.40 g, 95%).

TLC R$_f$ 0.4 (ethyl acetate)

Intermediate 40

2-Methylene-3-phenylpropanoic Acid

From dibenzyl benzylmalonate (10 g) as a colourless oil (4.5 g, 100%).

TLC R$_f$ 0.34 (diethyl ether)

Intermediate 41

2-Methylenepentanoic Acid

From intermediate 32 (25.9 g) as a colourless oil (5.8 g, 64%).

TLC R$_f$ 0.33 (ethyl acetate)

Intermediate 42

1-Methylenebutane-1,4-dicarboxylic Acid

A solution of intermediate 33 (3.79 g) in ethanol (10 ml) was treated with water (50 ml) and potassium hydroxide (4.65 g). The reaction was heated at 100° C. for two hours and the organic solvent removed in vacuo. The aqueous residue was washed with ethyl acetate (50 ml) separated and the basic layer acidified to pH 1 with 6 M hydrochloric acid. The product was extracted with ethyl acetate (3×100 ml), the extracts combined, dried over magnesium sulfate and filtered. The filtrate was evaporated in vacuo and the residue treated with piperidine (0.7 g) at room temperature. After 30 minutes the reaction was treated with formaldehyde (37% solution in water, 3.3 ml), stirred for two hours at room temperature and then heated at 80° C. for two hours. The mixture was cooled, the solvent removed in vacuo and the residue partitioned between ethyl acetate (100 ml) and 10% aqueous citric acid (50 ml). the organic layer was washed with water (50 ml), brine (50 ml), dried over magnesium sulfate, filtered and the filtrate evaporated in vacuo. The residue was purified by column chromatography on silica gel eluting with 50% ethyl acetate in hexane to yield the title compound as a white solid (1.0 g, 49%).

TLC $R_f$ 0.28 (50% ethyl acetate in hexane)

Intermediate 43

2-Methylene-3-methylbutanoic Acid

Piperidine (6 ml) was added to a solution of isopropyl-malonic acid (5 g) in dioxan (70 ml) and the reaction was stirred for 0.5 h. Formaldehyde (37% aqueous, 6 ml) was added and the reaction was stirred for 16 hours. The reaction was heated to 80° C. for 2 h, cooled to room temperature, and partitioned between ethyl acetate and water. The aqueous phase was acidified to pH 1 and extracted with dichloromethane. Combined organic phases were dried and the solvents removed in vacuo to give the title compound as a colourless oil (3.1 g, 79%).

TLC $R_f$ 0.5 (5% methanol/dichloromethane)

Similarly prepared was:

Intermediate 44

2-Methylene-4-(pyrid-2-yl)butanoic Acid

From 2-(2-pyridylethyl)malonic acid (2.5 g) as colourless solid (1.80 g, 90%).

TLC $R_f$ 0.3 (EtOAc).

Intermediate 45

2-Bromomethyl-5-phthalimidopentanoic Acid

Intermediate 34 (1.0 g) was treated with 45% hydrogen bromide in acetic acid (30 ml) at room temperature. After three hours the solution was poured into water (300 ml) and the product extracted with ethyl acetate (3×100 ml). The extracts were combined, washed with water (100 ml), brine (100 ml), dried over magnesium sulfate, filtered and the filtrate evaporated in vacuo. The residue was dried by azeotrope with toluene (2×10 ml) to yield the title compound as a white solid (1.3 g, 100%).

TLC $R_f$ 0.34 (50% ethyl acetate-hexane)

Similarly prepared were:

Intermediate 46

2-Bromomethyl-4-phthalimidobutanoic Acid

From intermediate 35 (4.7 g), as a white solid (5.3 g, 85%).

TLC $R_f$ 0.36 (50% ethyl acetate-hexane)

Intermediate 47

2-Bromomethyl-5-succinimidopentanoic Acid

From intermediate 36 (2.86 g) as colourless solid (2.50 g, 63%).

TLC $R_f$ 0.3 (ethyl acetate)

Intermediate 48

2-Bromomethyl-4-(3,4,4-trimethylhydantoin-1-yl)butanoic Acid

From intermediate 37 (1.5 g) as colourless solid (0.80 g, 45%).

TLC $R_f$ 0.2 (5% methanol-dichloromethane)

Intermediate 49

2-Bromomethyl-5-(3,4,4trimethylhydantoin-1-yl)-pentanoic Acid

From intermediate 39 (5.4 g) as a viscous oil (4.0 g, 56%).

TLC $R_f$ 0.35 (ethyl acetate)

Intermediate 50

2-Bromomethyl-3-phenylpropanoic Acid

From intermediate 40 (26.2 g) as a colourless oil (33.2 g, 86%).

TLC $R_f$ 0.45 (1:1 ethyl acetate-hexane)

Intermediate 51

2-(Bromomethyl)pentanoic Acid

From intermediate 41 (4.8 g) as a colourless oil (7.0 g, 85%).

TLC $R_f$ 0.36 (20% ethyl acetate—hexane)

Intermediate 52

2-Bromomethyl-5phenylpentanoic Acid

From intermediate 38 (3.4 g) as a colourless oil (4.2 g, 87%).

TLC $R_f$ 0.32 (20% ethyl acetate-hexane)

Intermediate 53

1-(Bromomethyl)butane-1,4-dicarboxylic Acid

From intermediate 42 (0:6 g), as a white solid (0.8 g, 88%)TLC $R_f$ 0.38 (50% ethyl acetate in hexane)

Intermediate 54

2-Bromomethyl-3-methylbutanoic Acid

From intermediate 43 (3.1 g) as a colourless oil (4.6 g, 87%).

MS 196 MH$^+$

Intermediate 55

2-Bromomethyl-4-(2-pyridyl)butanoic Acid Hydrobromide

Intermediate 44 (1.80 g) was dissolved in 48% HBr/acetic acid (20 ml) and stirred for 2 h, then evaporated in vacuo and

Intermediate 56

Methyl 2-(Bromomethyl)-5-phenylpentanoate

Intermediate 52 (5.0 g) was treated with a solution of diazomethane in diethyl ether. Removal of the solvent in vacuo gave the title compound as a colourless oil (5.2 g, 100%).

TLC $R_f$ 0.31 (5% ethyl acetate—hexane)

Intermediate 57

Methyl 2-Acetylsulfanylmethyl-5-phenylpentanoate

A solution of intermediate 56 in DMF was treated with potassium thioacetate (6.0 g) at 60° C. for 18 h. The mixture was added to water and extracted with ether, then the solvent was washed with water and brine, dried and evaporated to give the title compound as a brown oil (8.5 g, 90%).

TLC $R_f$ 0.80 (ether).

Intermediate 58

Methyl 2-Chlorosulfonylmethyl-5-phenylpentanoate

Chlorine was passed through a suspension of intermediate 57 (0.7 g) in iced water (20 ml) for 30 min. The yellow suspension was then extracted with dichloromethane and the solvent was washed with water, sodium metabisulfite and brine, then dried and evaporated to give a the title compound (0.7 g, 100%) as colourless oil.

TLC $R_f$ 0.45 (ether).

Intermediate 59

2-(4-Hydroxy-3,5-dimethylbenzoyl)benzoic Acid

Was prepared according to *Chem. Ber.*, 1983, 116, 970.

Intermediate 60

4-(4-Hydroxy-3,5-dimethylphenyl)-2-methyl-1(2H) phthalazinone

Was prepared according to *Chem. Ber.*, 1983, 116, 970.

Intermediate 61

1-tert-Butoxycarbonylpiperidine-4-thiol

Sodium borohydride (5.0 g) was added to a solution of intermediate 23 (5.1 g) in methanol (200 ml). The solution was stirred at room temperature for two hours and then evaporated in vacuo. The residue was carefully dissolved in water and citric acid added (5.0 g). The product was extracted with dichloromethane (2×100 ml), the extracts combined, dried over magnesium sulfate, filtered and the filtrate evaporated in vacuo to give the title compound as a pale yellow oil (4.70 g, 98%)

TLC $R_f$ 0.40 (ether).

Intermediate 62

2-(4-Benzoylphenylsulfanylmethyl)-5-phthalimidopentanoic Acid

A solution of intermediate 45 (1.0 g) in THF (20 ml) was purged with nitrogen for 5 minutes and treated with intermediate 15 (0.7 g) and triethylamine (1.0 ml). The mixture was stirred at room temperature for 24 hours and then the solvent removed in vacuo. The residue was partitioned between ethyl acetate (100 ml) and water (100 ml). The aqueous layer was extracted with ethyl acetate (50 ml), the extracts combined, washed with brine, dried over magnesium sulfate and filtered. The filtrate was evaporated in vacuo and the residue was purified by column chromatography on silica gel eluting with 50% ethyl acetate in hexane to yield the title compound (0.5 g, 35%) as a clear gum.

TLC $R_f$ 0.33 (50% ethyl acetate-hexane)

Similarly prepared were:

Intermediate 63

3-(4-Benzoylphenylsulfanyl)propanoic Acid

From intermediate 15 (1.5 g) and 3-bromopropionic acid (1.07 g), as a white solid (0.32 g, 16%).

TLC $R_f$ 0.05 (50% ethyl acetate-hexane)

Intermediate 64

2-(4-Acetylphenylsulfanylmethyl)-5-phenylpentanoic Acid

From intermediate 1 (0.37 g) and intermediate 52 (1.34 g) as an orange oil (0.5 g, 41%).

TLC $R_f$ 0.47 (5% methanol-dichloromethane)

Intermediate 65

2-(Thiazol-2-ylsulfanylmethyl)-5-phenylpentanoic Acid

From intermediate 52 (1.16 g) and 2-mercaptothiazole (0.5 g) as a colourless oil (0.125 g, 9%).

TLC $R_f$ 0.6 (5% methanol-dichloromethane)

Intermediate 66

2-(4-N,N-Dimethylcarbamoylphenylsulfanylmethyl)-5-phenylpentanoic Acid

From intermediate 52 (0.2 g) and intermediate 4 (0.344 g) as a colourless oil (0.29 g, 59%).

TLC $R_f$ 0.22 (5% methanol-dichloromethane)

Intermediate 67

2-(4-Methoxybenzenesulfanylmethyl)-5-phenylpentanoic Acid

From 4-methoxybenzenethiol (0.556 g) and intermediate 52 (1.08 g) as a pale yellow oil (1.021 g, 78%).

TLC $R_f$ 0.80 (50% ethyl acetate-hexane)

Intermediate 68

2-(4-Methoxyphenylsulfanylmethyl)-5-phthalimidopentan-oic Acid

From intermediate 45 (1.0 g) and 4-methoxybenzenethiol (0.45 g) as a clear gum (1.1 g, 94%).

TLC $R_f$ 0.62 (4% methanol-dichloromethane)

Intermediate 69

2-(4-Methoxyphenylsulfanylmethyl)-4-phthalimidopentanoic Acid

From intermediate 46 (1.0 g) and 4-methoxybenzenethiol (0.47 g) as a clear gum (0.92 g, 78%).

TLC $R_f$ 0.19 (2% methanol-dichloromethane)
TLC $R_f$ 0.41 (50% ethylacetate-hexane)

Intermediate 70

5-Phenyl-2-(phenylsulfanylmethyl)pentanoic Acid

From benzenethiol (0.107 g) and intermediate 52 (0.248 g) as a milky white oil (0.223 g, 82%).
TLC $R_f$ 0.46 (4:1 hexane-ethyl acetate)

Intermediate 71

2-(2-Methoxyphenylsulfanylmethyl)-5-phenylpentanoic Acid

From 2-methoxybenzenethiol (0.324 g) and intermediate 52 (0.597 g) as a colourless oil (0.539 g, 74%).
TLC $R_f$ 0.29 (20% ethyl acetate-hexane)

Intermediate 72

2-(3-Methoxyphenylsulfanylmethyl)-5-phenylpentanoic Acid

From 3-methoxybenzenethiol (0.318 g) and intermediate 52 (0.585 g) as a colourless oil (0.662 g, 93%).
TLC $R_f$ 0.29 (20% ethyl acetate-hexane)

Intermediate 73

2-(4-Carbamoylmetholoxy)phenylsulfanylmethyl)-5-phenylpentanoic Acid

From intermediate 11 (0.503 g) and intermediate 52 (0.744 g) as a white solid (0.884 g, 86%).
TLC $R_f$ 0.41 (5% methanol-dichloromethane)

Intermediate 74

2-(4-Benzoylphenylsulfanylmethyl)-5-phenylpentanoic Acid

From intermediate 52 (5.6 g) and intermediate 15 (4.6 g) as a pale amber oil (7.5 g, 92%).
TLC $R_f$ 0.32 (3:1 hexane-ethyl acetate)

Intermediate 75

2-(Pyrid-4-ylsulfanylmethyl)-5-phenylpentanoic Acid

From 4-mercaptopyridine (0.33 g) and intermediate 52 (0.84 g) as a white solid (0.53 g, 58%).
TLC $R_f$ 0.45 (ethyl acetate)

Intermediate 76

2-(4-Methoxyphenylsulfanylmethyl)-5-succinimidopentanoic Acid

From intermediate 47 (1.5 g) and 4-methoxybenzenethiol (0.71 g) as a colourless oil (1.56 g, 80%).
TLC $R_f$ 0.3 (diethyl ether)

Intermediate 77

2-(4-Benzoylphenylsulfanylmethyl)-5-succinimidopentanoic Acid

From intermediate 15 (0.21 g) and intermediate 47 (0.29 g) as a white solid (0.34 g, 80%).
TLC $R_f$ 0.27 (ethyl acetate)

Intermediate 78

2-(4-Acetamidophenylsulfanylmethyl)-5-phenylpentanoic Acid

From 4-acetamidobenzenethiol (0.17 g) and intermediate 52 (0.28 g) as a colourless oil (0.25 g, 45%).
TLC $R_f$ 0.5 (diethyl ether)

Intermediate 79

2-((1-Methylimidazol-2-yl)methylsulfanyl)-5-phenylpentanoic Acid

From 2-mercapto-1-methylimidazole (1.14 g) and intermediate 52 (2.8 g) as a white solid (0.5 g, 16%).
TLC $R_f$ 0.30 (6methanol-dichloromethane)

Intermediate 80

2-(4-Methoxyphenylsulfanylmethyl)-5-(3,3,4-trimethylhydantoin-1-yl)pentanoic Acid From 4-methoxybenzenethiol (0.28 g) and intermediate 49 (0.68 g) as a white solid (0.64 g, 80%).
TLC $R_f$ 0.4 (ethyl acetate)

Intermediate 81

2-(4-Methoxyphenylsulfanylmethyl-4(3,3,4-trimethylhydantoin-1-yl)butanoic Acid

From intermediate 48 (0.48 g) and 4-methoxybenzenethiol (0.21 g) as a white solid (0.49 g, 87%).
TLC $R_f$ 0.31 (ethyl acetate)

Intermediate 82

2-(4-Methoxyphenylsulfanylmethyl)-3-phenylpropanoic Acid

From intermediate 50 (2.43 g) and 4-methoxybenzenethiol (1.4 g) as a white solid (2.95 g, 98%).
TLC $R_f$ 0.55 (ethyl acetate)

Intermediate 83

Ethyl 4-(4-Methoxyphenyl)sulfanylbutanoate

From 4-methoxythiophenol (10.0 g) and ethyl 4-bromobutyrate (10.2 ml) as a colourless liquid (16.7 g, 92%).
TLC $R_f$ 0.5 (3:1 hexane-diethyl ether)

Intermediate 84

2-(4-Methoxyphenylsulfanylmethyl)-pentanoic Acid

From intermediate 51 (2.0 g) and 4-methoxybenzenethiol (1.3 ml) as a yellow oil (2.6 g, 99%).
TLC $R_f$ 0.40 (50% ethyl acetate-hexane)

Intermediate 85

1-(4-Methoxyphenylsulfanylmethyl)butane-1,4-dicarboxylic Acid

From intermediate 53 (0.6 g) and 4-methoxybenzenethiol (0.38 g) as a clear gum (0.57 g, 76%).
TLC $R_f$ 0.36 (50% ethyl acetate in hexane)

Intermediate 86

3-Methyl-2-(4-methoxyphenylsulfanylmethyl) butanoic Acid

From intermediate 54 (3.5 g) and 4-methoxybenzenethiol (2.51 g) as a colourless oil (3.26 g, 71%).

TLC $R_f$ 0.25 (5% methanol/dichloromethane)

Intermediate 87

2-[(Benzo(1,3)dioxole-5-yl)sulfanylmethyl]-5-phenylpentanoic Acid

From intermediate 16 (2.0 g) and intermediate 52 (3.52 g) as a yellow-brown oil (3.78 g, 85%).

TLC $R_f$ 0.52 (5% methanol/dichloromethane)

Intermediate 88

2-[(4-Trifluoromethoxyphenylsulfanyl)methyl]-5-(1,5,5-trimethylhydantoin-3-yl)pentanoic Acid From intermediate 49 (0.51 g) and 4-trifluoromethoxybenzenethiol (0.29 g) as a colourless oil (0.47 g, 70%).

TLC $R_f$ 0.32 (50% hexane/ethyl acetate with trace acetic acid)

Intermediate 89

2-[(4-Trifluoromethoxyphenylsulfanyl)methyl] pentanoic Acid

From intermediate 51 (2.00 g) and 4-trifluoromethoxybenzenethiol (1.99 g) as a pale yellow oil (2.78 g, 88%).

TLC $R_f$ 0.50 (hexane/ethyl acetate/acetic acid (200:50:3))

Intermediate 90

2-(Quinolin-2-ylsulfanyl)methyl-5-phenylpentanoic Acid

From 2-mercaptoquinoline (256 mg) and intermediate 52 (0.3 g) as a colourless solid (0.3 g, 50%).

TLC $R_f$ 0.40 (ethyl acetate)
MS 352 [MH$^+$]

Intermediate 91

2-(4-Benzoylphenyl)sulfanylmethyl-4-(3,3,4-trimethylhydantoin-1-yl)butanoic Acid From 4-mercaptobenzophenone (0.17 g) and intermediate 48 (0.20 g) as white solid (0.20 g, 85%).

TLC $R_f$ 0.50 (ether)
MS 470 [MH$^+$]

Intermediate 92

2-(4-Benzoylphenyl)sulfanylmethyl-5-(3,3,4-trimethylhydantoin-1-yl)pentanoic acid From 4-mercaptobenzophenone (0.34 g) and intermediate 49 (0.40 g) as a pale amber oil (0.52 g, 62%).

TLC $R_f$ 0.45 (ethyl acetate)
MS 468 [MH$^+$]

Intermediate 93

2-(4-Benzoylphenyl)sulfanylmethyl-3-phenylpropanoic Acid

From 4-mercaptobenzophenone (0.85 g) and intermediate 50 (0.80 g) as a pale yellow gum (1.01 g, 59%).

TLC $R_f$ 0.60 (ether)
MS 372 [MH$^+$]

Intermediate 94

2-(4-Methoxyphenyl)sulfanylmethyl-4-(pyrid-2-yl) butanoic Acid

From intermediate 55 (1.0 g) and 4-methoxybenzenethiol (0.42 g) as a colourless oil (0.25 g, 25%).

TLC $R_f$ 0.25 (10% MeOH/dichloromethane).
MS 318 [MH$^+$]

Intermediate 95

2-(4-(4-Pyridinoyl)phenylsulfanyl)methyl-5-phenylpentanoic Acid

From intermediate 24 (1.1 g) and intermediate 52 (1.4 g) as white solid (1.62 g, 80%).

TLC $R_f$ 0.6 (EtOAc).
MS 406 [MH$^+$]

Intermediate 96

2-(4-(2-Thienoyl)phenylsulfanyl)methyl-5-phenylpentanoic Acid

From intermediate 25 (1.3 g) and intermediate 52 (1.4 g) as white solid (1.8 g, 85%).

TLC $R_f$ 0.60 (ether).
MS 410 [MH$^+$]

Intermediate 97

2-(4-(4-Pyridinoyl)phenyl)sulfanylmethyl-5-(3,3,4-trimethylhydantoin-1-yl)pentanoic Acid From intermediate 24 (0.21 g) and intermediate 49 (0.34 g) as white solid (0.25 g, 65%).

TLC $R_f$ 0.50 (10% MeOH/dichloromethane).
MS 469 [MH$^+$]

Intermediate 98

2-(4-(2-Thienoyl)phenyl)sulfanylmethyl-5-(3,3,4-trimethylhydantoin-1-yl)pentanoic Acid From intermediate 25 (0.66 g) and intermediate 49 (1.0 g) as white solid (1.3 g, 90%).

TLC $R_f$ 0.70 (EtOAc).

Intermediate 99

2-(4-Hydroxyphenyl)sulfanylmethyl-5-phenylpentanoic Acid

From 4-mercaptophenol (1.26 g) and intermediate 52 as colourless oil (3.0 g, 95%).

TLC $R_f$ 0.63 (ether).

Intermediate 100

2-((Quinolin-8-yl)sulfanylmethyl)-5-phenylpentanoic Acid

From 8-quinoline thiol (120 mg) and intermediate 52 (170 mg) as colourless solid (105 mg, 50%).

TLC $R_f$ 0.50 (ether).

Intermediate 101

2-(Furan-2-ylmethylsulfanyl)methyl-5-phenylpentanoic Acid

Potassium tert-butoxide (415 mg) was added to a stirred solution of furfuryl thiol (0.186 ml) in dichloromethane (20 ml) at 0° C. under a nitrogen atmosphere. The mixture was stirred for 3 min before a solution of intermediate 37 (500 mg) in dichloromethane (5 ml) was added. The mixture was allowed to warm to room temperature and stirred for 6 h before being poured into HCl (0.5 M, 100 ml). The mixture was extracted with ethyl acetate (2×100 ml). The combined organic phases were washed with brine and dried (MgSO$_4$). The solvent was removed in vacuo to give the title compound as a yellow oil (560 mg, 99%).

TLC R$_f$ 0.3 (4:1 hexane-ethyl acetate)
Similarly prepared were:

Intermediate 102

2-(Cyclopentylsulfanyl)methyl-5-phenylpentanoic Acid

From intermediate 52 (500 mg), and cyclopentanethiol (0.198 ml) as a pale yellow oil (540 mg, 99%).

TLC R$_f$ 0.4 (4:1 hexane-ethyl acetate).

Intermediate 103

2-(Benzylsulfanylmethyl)-5-phenylpentanoic Acid

From benzylmercaptan (0.059 g) and intermediate 52 (0.128 g) as a colourless oil (0.116 g, 78%).

TLC R$_f$ 0.49 (hexane-ethyl acetate-acetic acid (200:50:3)

Intermediate 104

5-Phenyl-2-[(tetrahydropyran-4-ylsulfanyl)methyl]-pentanoic Acid

From intermediate 18 (0.40 g) and intermediate 52 (0.700 g) as a pale yellow oil (0.99 g, 94%).

TLC R$_f$ 0.50 (hexane/diethyl ether (1:1))
MS 373 (M+NH$_4^+$)

Intermediate 105

2-(2-Phenylethylsulfanylmethyl)-5-phenylpentanoic Acid

Potassium hexamethyldisilazide (0.5 M in toluene, 20 ml) was added to a solution of phenethyl mercaptan (0.7 g) in THF (50 ml) at −78° C. and the solution was stirred for 10 min, then a solution of intermediate 52 (1.4 g) in THF (10 ml) was added dropwise and the mixture was stirred for 3 hours, warming to room temperature. The mixture was added to water and the solution was washed with diethyl ether, acidified with acetic acid and extracted with ether. The ether layer was washed with water and brine, dried and evaporated and the residue purified by column chromatography, eluting with 20% ethyl acetate in hexane to give the title compound (1.30 g, 78%) as a colourless oil.

TLC R$_f$ 0.3 (20% ethyl acetate-hexane).
Similarly prepared were:

Intermediate 106

2-(3-Phenylpropylsulfanyl)methyl-5-phenylpentanoic Acid

From phenpropyl mercaptan (1.5 g) and intermediate 52 (2.8 g) as colourless oil (1.6 g, 50%).

TLC R$_f$ 0.86 (ether).

Intermediate 107

2-(2-Methylpropylsulfanylmethyl)-5-phenylpentanoic Acid

From isobutyl mercaptan (0.9 g) and intermediate 52 (2.8 g) as a colourless oil (2.6 g, 93%).

TLC R$_f$ 0.83 (diethyl ether)

Intermediate 108

2-(1-Benzoylpiperdine-4-yl)sulfanylmethyl-5-phenylpentanoic Acid

From intermediate 21 (2.0 g) and intermediate 52 (2.0 g) as colourless oil (1.6 g).

TLC R$_f$ 0.34 (ether)

Intermediate 109

2-((1-tert-Butyloxycarbonyl)piperidin-4-yl)sulfanylmethyl-5-phenylpentanoic Acid From intermediate 61 (4.2 g) and intermediate 52 (5.2 g) as colourless oil (4.5 g, 53%).

TLC R$_f$ 0.3 (1:1 ether/hexanes).

Intermediate 110

2-(4-Methoxyphenylsulfanylmethyl)-5-(methoxycarbonyl)pentanoic Acid

A solution of intermediate 85 (0.5 g) in methanol (10 ml) was treated with 4-toluenesulfonic acid (16 mg) at room temperature. The mixture was heated at 40° C. under nitrogen for 2 h, then allowed to cool and the solvent was removed in vacuo. The residue was partitioned between ethyl acetate (100 ml) and water (50 ml). The organic layer was separated, dried over magnesium sulfate, filtered and the filtrate evaporated in vacuo. The residue was purified by column chromatography on silica gel eluting with 40% ethyl acetate in hexane to give the title compound as a white solid (0.38 g, 72%).

TLC R$_f$ 0.48 (50% ethyl acetate in hexane)

Intermediate 111

Methyl 2-(4-Bromophenylsulfanylmethyl)-5-phenylpentan-oate

A solution of intermediate 46 (4.70 g) and 4-bromothiophenol (4.79 g) in tetrahydrofuran (50 ml) was treated with 10% sodium hydroxide in water (4.0 ml) and heated at reflux for 3 hours. The reaction mixture was concentrated to an aqueous residue in vacuo and partitioned between diethyl ether (250 ml) and water (150 ml). The organic phase was dried over magnesium sulfate, concentrated onto silica in vacuo and purified by chromatography on silica eluting with 20% ethyl acetate in hexane to give the title compound as a colourless oil (6.46 g, 71%).

TLC R$_f$ 0.2 (3% ethyl acetate-heptane)

Intermediate 112

Methyl 3-(4-Methoxyphenylsulfanyl)propanoate

4-Methoxythiophenol (4.80 g) was added to a stirred solution of methyl acrylate (3.08 ml) in dichloromethane (60 ml) at 0° C. Potassium carbonate (4.72 g) was added and the mixture was allowed to warm to room temperature overnight. The mixture was filtered over a plug of Celite® and the solvent was removed in vacuo to give the title compound as a yellow liquid (7.70 g, 100%).

TLC $R_f$ 0.3 (2:1 hexane-ethyl acetate)

Similarly prepared was:

Intermediate 113

Methyl 3-(4-Bromophenylsulfanyl)propanoate

From 4-bromothiophenol (6.26 g) as a yellow oil (8.75 g, 96%).

TLC $R_f$ 0.5 (60% ethyl acetate-hexane)

Intermediate 114

Methyl 3-[4-(Chlorophenyl)phenylsulfanylmethyl]-propanoate

A solution of intermediate 113 (2.80 g) and 4-chlorobenzeneboronic acid (1.91 g) in THF (80 ml) at room temperature under a nitrogen atmosphere was treated with dichloro bis(triphenylphosphine)palladium(II) (1.43 g). Aqueous sodium carbonate solution (2 M) was added and the mixture was heated at reflux overnight. The mixture was cooled to room temperature and the THF was removed in vacuo. The residue was dissolved in diethyl ether, washed with brine and dried ($MgSO_4$). The solvent was removed in vacuo and the residue was eluted from a column of silica with 10% diethyl ether in hexane to provide the title compound as a white solid (700 mg, 22%).

TLC $R_f$ 0.2 (5% diethyl ether-hexane)
MS 323 $MNH_4^+$

Similarly prepared was:

Intermediate 115

Methyl 2-[4-(4-Chlorophenyl)phenylsulfanyl)methyl]-5-phenylpentanoate

From intermediate 111 (5.20 g) and 4-chlorobenzeneboronic acid (2.48 g), as a colourless oil (4.07 g, 74%).

TLC $R_f$ 0.3 (10% diethyl ether-heptane)
MS 425 $MH^+$

Intermediate 116

3-(4-Bromophenylsulfanyl)propanoic Acid

A solution of intermediate 113 (1.01 g) in THF (15 ml) and water (5 ml) at 0° C. was treated with lithium hydroxide (154 mg). The mixture was allowed to warm slowly to room temperature and stirred overnight. The mixture was acidified to pH 5 with 10% aqueous citric acid and diluted with water (75 ml) and ethyl acetate (100 ml). The aqueous phase was extracted with ethyl acetate (100 ml) and the combined organic phases were washed with brine and dried ($MgSO_4$). The solvent was removed in vacuo to give the title compound as a white solid (890 mg, 93%).

TLC $R_f$ 0.3 (1:2 hexane-ethyl acetate)
MS 261 $MH^+$

Similarly prepared were:

Intermediate 117

3-[4-(Chlorophenyl)phenylsulfanyl]propanoic Acid

From intermediate 114 (450 mg), as a white solid (430 mg, 100%).

TLC $R_f$ 0.3 (10% diethyl ether-hexane)
MS 244

Intermediate 118

3-(4-Methoxyphenyl)sulfanylpropanoic Acid

From intermediate 112 (5.00 g), as a white solid (4.40 g, 94%).

TLC $R_f$ 0.4 (1:1 hexane-ethyl acetate)
MS 330 $MNH_4^+$

Intermediate 119

3-(4-Methoxyphenylsulfanylmethyl)-6-phenylhexanoic Acid

From intermediate 8 (240 mg), as a colourless oil (234 mg, 100%).

TLC $R_f$ 0.1 (3:1 hexane-diethyl ether)

Intermediate 120

4-(4-methoxyphenylsulfanyl)butanoic Acid

From intermediate 83 (5.00 g), as a white solid (4.10 g, 92%).

TLC $R_f$ 0.1 (3:1 hexane-diethyl ether)

Intermediate 121

2-[4-(4-Chlorophenyl)phenylsulfanylmethyl]-5-phenylpentanoic Acid

From intermediate 115 (1.57 g), as a white solid (1.42 g, 93%).

TLC $R_f$ 0.3 (10% diethyl ether-heptane)
MS 428 $MNH_4^+$

Example 1

2-(4-Benzoylphenylsulfinylmethyl)-5-phenylpentanoic Acid

A solution of intermediate 74 (84 mg) in dichloromethane (10 ml) was cooled to 0° C. and treated with 4-chloroperbenzoic acid (73 mg). The reaction was warmed to room temperature and stirred for 3 hours. The reaction mixture was concentrated onto silica in vacuo and purified by chromatography on silica eluting with 1% acetic acid and 1% methanol in dichloromethane to give the title compound as a colourless oil (42 mg, 48%).

TLC $R_f$ 0.10 (30% ethyl acetate-hexane)
MS 421 $MH^+$

Similarly prepared was:

Intermediate 122

3-(4-Methoxyphenylsulfinyl)propanoic Acid

From intermediate 118 (1:00 g), as a white solid (688 mg, 63%).

TLC $R_f$ 0.1 (1:2 hexane-ethyl acetate)
MS 229 $MH^+$

Example 2

2-(4-Benzoylphenylsulfonylmethyl)-5-phthalimido-pentanoic Acid

A solution of intermediate 62 (0.4 g) in methanol (50 ml) was treated at room temperature with a solution of Oxone®

(0.52 g) in water (10 ml). The mixture was stirred for 24 hours and the organic solvent removed in vacuo. The residue was diluted with water (100 ml) and extracted with ethyl acetate (3×100 ml). The organic extracts were combined, washed with brine (40 ml), dried over magnesium sulfate and filtered. The filtrate was evaporated in vacuo and the residue was purified by column chromatography on silica gel eluting with 2% methanol in dichloromethane to yield the title compound as a white solid (0.37 g, 87%).

TLC $R_f$ 0.24 (2% methanol-dichloromethane)
MS 506 MH$^+$
Similarly prepared were:

Intermediate 123

3-(4-Benzoylphenylsulfonyl)propanoic Acid

From intermediate 63 (0.257 g) as a white solid (0.20 g, 69%)
TLC $R_f$ 0.3 (ethyl acetate)
MS 319 MH$^+$

Example 3

2-(4-Acetylphenylsulfonylmethyl)-5-phenylpentanoic Acid

From intermediate 64 (0.12 g) as a cream solid (0.094 g, 72%).
TLC $R_f$ 0.43 (10% methanol-dichloromethane)
MS 374 MH$^+$

Intermediate 124

2-(2-Thiazolysulfonylmethyl)-5-phenylpentanoic Acid

From intermediate 65 (0.125 g) as a colourless oil (0.094 g, 67%).
TLC $R_f$ 0.4 (5% methanol-dichloromethane)
MS 341 MH$^+$

Example 4

2(4-N,N-Dimethylcarbamoylsulfonylmethyl)-5-phenyl pentanoic Acid

From intermediate 66 (0.289 g) as a colourless oil (0.250 g, 83%).
TLC $R_f$ 0.36 (10% methanol-dichloromethane)
MS 404 MH$^+$

Example 5

2-(4-Methoxyphenylsulfonylmethyl)-5-phthalimido-pentanoic Acid

From intermediate 68 (0.9 g), as a white solid (0.7 g, 72%).
TLC $R_f$ 0.58 (5% methanol-dichloromethane)
MS 432 MH$^+$

Example 6

2-(4-Methoxyphenylsulfonylmethyl)-4-phthalimido-butanoic Acid

From intermediate 69 (0.9 g), as a white solid (0.8 g, 82%).

TLC $R_f$ 0.19 (4% methanol-dichloromethane)
MS 418 MH$^+$

Intermediate 125

3-(4-Bromophenylsulfonyl)propanoic Acid

From intermediate 116 (260 mg) as a white solid (241 mg, 83%).
TLC $R_f$ 0.3 (1:2 hexane-ethyl acetate)
MS 294 MH$^+$

Intermediate 126

3-[4-(Chlorophenyl)phenylsulfonyl]propanoic Acid

From intermediate 117 (195 mg) as a white solid (196 mg, 90%).
TLC $R_f$ 0.2 (10% diethyl ether-hexane)
MS 341 MH$_4^+$

Intermediate 127

3-(4-Methoxyphenylsulfonyl)propanoic Acid

From intermediate 118 (1.00 g) as a white solid (1.13 g, 98%).
TLC $R_f$ 0.2 (1:2 hexane-ethyl acetate)
MS 262 MH$_4^+$

Example 7

2-(Furan-2-ylmethylsulfonylmethyl)-5-phenylpentanoic Acid

From intermediate 101 (560 mg), as a colourless oil (401 mg, 64%).
TLC $R_f$ 0.3 (3:1 hexane-ethyl acetate)
MS 354 MNH$_4^+$

Example 8

2-(Cyclopentylsulfonylmethyl)-5-phenylpentanoic Acid

From intermediate 102 (540 mg), as a colourless oil (387 mg, 64%).
TLC $R_f$ 0.3 (3:1 hexane-ethyl acetate)
MS 342 MNH$_4^+$

Example 9

3-(4-Methoxyphenylsulfonylmethyl)-6-phenylhexanoic Acid

From intermediate 119 (230 mg), as a colourless oil (157 mg, 62%).
TLC $R_f$ 0.2 (1:2 hexane-ethyl acetate)
MS 394 MNH$_4^+$

Example 10

2-(4-Methoxyphenylsulfonylmethyl)-5-phenylpentanoic Acid

From intermediate 67 (0.50 g) as a white solid (0.52 g, 95%).
TLC $R_f$ 0.61 (50% ethyl acetate-hexane)
MS 380 MNH$_4^+$

Example 11

2-Benzylsulfonylmethyl)-5-phenylpentanoic Acid

From intermediate 103 (0.569 g), as a white solid (0.613 g, 98%).
TLC $R_f$ 0.53 (50% ethyl acetate-hexane)
MS 364 $MNH_4^+$

Example 12

5-Phenyl-2-(phenylsulfonylmethyl)pentanoic Acid

From intermediate 70 (0.494 g), as a white solid (0.543 g, 100%).
TLC $R_f$ 0.52 (50% ethyl acetate-hexane)
MS 348 $MNH_4^+$

Example 13

2-(2-Methoxybenzenesulfonylmethyl)-5-phenylpentanoic Acid

From intermediate 71 (0.539 g), as a colourless oil (0.561 g, 95%).
TLC $R_f$ 0.47 (50% ethyl acetate-hexane)
MS 380 $MNH_4^+$

Example 14

2-(3-Methoxyphenylsulfonylmethyl)-5-phenylpentanoic Acid

From intermediate 72 (0.610 g), as a colourless oil (0.617 g, 92%).
TLC $R_f$ 0.58 (50% ethyl acetate-hexane)
MS 380 $MNH_4^+$

Intermediate 128

2-(4-Carbamoylmethyloxy)phenylsulfonylmethyl)-5-phenylpentanoic Acid

From intermediate 73 (0.864 g), as a white solid (0.653 g, 70%).
TLC $R_f$ 0.29 (5% methanol-dichloromethane)
MS 423 $MNH_4^+$

Example 15

2-(4-Benzoylphenylsulfonylmethyl)-5-phenylpentanoic Acid

From intermediate 74 (7.5 g) as a colourless solid (7.4 g, 91%).
TLC $R_f$ 0.3 (1:1 ethyl acetate-hexane).
MS 437 $MH^+$

Example 16

2-(Pyrid-4-ylsulfonylmethyl)-5-phenylpentanoic Acid

From intermediate 75 (0.52 g) as a white solid (0.55 g, 96%).
TLC $R_f$ 0.25 (5% methanol-dichloromethane).
MS 334 $MH^+$

Intermediate 129

2-((4-Acetylamino)phenylsulfonylmethyl)-5-phenylpentanoic Acid

From intermediate 78 (0.20 g) as a colourless solid (0.12 g, 56%).
TLC $R_f$ 0.3 (ethyl acetate).
MS 390 $MH^+$

Intermediate 130

2-((1-Methylimidazol-2-yl)sulfonylmethyl)-5-phenylpentanoic Acid

From intermediate 79 (0.5 g) as a white solid (0.35 g, 64%).
TLC $R_f$ 0.2 (6% methanol-dichloromethane).
MS 337 $MH^+$

Example 17

2-(2-Phenylethylsulfonylmethyl)-5-phenylpentanoic Acid

From intermediate 105 (1.35 g) as a white solid (1.40 g, 94%).
TLC $R_f$ 0.5 (diethyl ether).
MS 361 $MH^+$

Example 18

2-((2-Methylpropyl)sulfonylmethyl)-5-phenylpentanoic Acid

From intermediate 107 (2.6 g) as a white solid (1.70 g, 59%).
TLC $R_f$ 0.5 (40% diethyl ether-hexane).
MS 312 $M^+$

Example 19

2-(4-Methoxyphenylsulfonylmethyl)-5-succinimidopentanoic Acid

From intermediate 76 (1.56 g) as a white solid (1.4 g, 82%).
TLC $R_f$ 0.15 (ethyl acetate)
MS 383 $M^+$

Example 20

2-(4-Benzoylphenyl)sulfonylmethyl-5-succinimidopentanoic Acid

From intermediate 77 (0.34 g) as a white solid (0.28 g, 78%).
TLC $R_f$ 0.2 (ethyl acetate)
MS 457 $M^+$

Example 21

2-(4-Methoxyphenylsulfonylmethyl)-5-(3,3,4-trimethylhydantoin-1-yl)pentanoic Acid From intermediate 80 (0.8 g) as a white solid (0.6 g, 70%).
TLC $R_f$ 0.4 (6% methanol-dichloromethane)
MS 427 $M^+$

Example 22

2-(4-Methoxyphenylsulfonylmethyl)-4-(3,3,4-trimethylhydantoin-1-yl)butanoic Acid From intermediate 81 (0.57 g) as a white solid (0.50 g, 79%).

TLC R$_f$0.35 (10% methanol-dichloromethane)
MS 413 MH$^+$

Example 23

2-(4-Methoxyphenylsulfonylmethyl)-3-phenylpropanoic Acid

From intermediate 82 (2.95 g) as a white solid (3.0 g, 90%). TLC R$_f$0.43 (ethyl acetate)
MS 334 M$^+$

Intermediate 131

4-(4-Methoxyphenylsulfonyl)butanoic acid

From intermediate 120 (1.00 g), as a white solid (1.12 g, 98%). TLC R$_f$0.2 (2:1 hexane-ethyl acetate)
MS 259 MH$^+$

Example 24

2-[4-(4-Chlorophenyl)phenylsulfonyl)methyl]-5-phenylpentanoic Acid

From intermediate 121 (1.24 g), as a white solid (1.01 g, 75%).
TLC R$_f$0.2 (10% diethyl ether-heptane)
MS 443 MH$^+$

Example 25

2-[4-Methoxyphenylsulfonylmethyl]pentanoic Acid

From intermediate 84 (2.6 g) as a white solid (2.2 g, 74%).
TLC R$_f$0.32 (5% methanol-dichloromethane)
MS 287 (M+H).

Intermediate 132

2-(4-Methoxyphenylsulfonylmethyl)-5-(methoxycarbonyl)pentanoic Acid

From intermediate 110 (0.3 g), as a white solid (0.2 g, 61%)
TLC R$_f$0.19 (50% ethyl acetate in hexane)
MS 345 MH$^+$

Example 26

3-Methyl-2-(4-methoxyphenylsulfonylmethyl)butanoic Acid

From intermediate 86 (3.26 g) as a white solid (2.3 g, 63%)
TLC R$_f$0.43 (10% methanol/dichloromethane)

Intermediate 133

2-(Benzo[1,3]dioxole-5-yl)sulfonylmethyl)-5-phenylpentanoic Acid

From intermediate 87 as a colourless oil (3.4 g, 81%)
TLC R$_f$0.48 (10% methanol/dichloromethane)

Example 27

2-[(4-Trifluoromethoxyphenylsulfonyl)methyl]-5-(1,5,5-trimethylhydantoin-3-yl)pentanoic Acid From intermediate 88 (0.47 g) as a white solid (0.49 g, 96%).
TLC R$_f$0.43 (hexane/ethyl acetate (1:2) with trace acetic acid)
MS 481 (MH$^+$)

Example 28

2-[4-(4-Trifluoromethoxyphenylsulfonyl)methyl]pentanoic Acid

From intermediate 89 (2.77 g) as a white solid (2.79 g, 91%).
TLC R$_f$0.73 (50% hexane/ethyl acetate with trace acetic acid)
MS 358 (MH+NH$_4^+$)

Intermediate 134

5-Phenyl-2-((tetrahydropyran-4-ylsulfonyl)methyl)pentanoic Acid

From intermediate 104 (0.99 g), as a waxy white solid (0.62 g, 57%).
TLC R$_f$0.10 (ethyl acetate/hexane/acetic acid (49:49:2))

Example 29

2-((Quinolin-2-yl)sulfanylmethyl)-5-phenylpentanoic Acid

From intermediate 90 (0.2 g) as a pale yellow gum (0.10 g).
TLC R$_f$0.53 (60% EtOAc-hexanes).
MS 384 (MH$^+$).

Example 30

2-(4-Benzoylphenyl)sulfonylmethyl-4-(3,3,4-trimethylhydantoin-1-yl)butanoic Acid From intermediate 91 (0.3 g) as a white solid (0.20 g, 66%).
TLC R$_f$0.54 (10% MeOH/dichloromethane)
MS 486 (M$^+$)

Example 31

2-(4-Benzoylphenyl)sulfonylmethyl-5-(3,3,4-trimethylhydantoin-1-yl)pentanoic Acid From intermediate 92 (0.6 g) as a white solid (0.25 g, 40%)
TLC R$_f$0.50 (10% MeOH/dichloromethane)
MS 500 (MH$^+$)

Example 32

2-((4-Benzoylphenylsulfonyl)methyl)-3-phenylpropanoic Acid

From intermediate 93 (1.10 g) as white solid (0.80 g, 60%).
TLC R$_f$0.60 (10% MeOH/dichloromethane).
MS 408 (M$^+$).

Intermediate 135

2-((1-Benzoylpiperidine-4-yl)sulfonylmethyl)-5-phenylpentanoic Acid

From intermediate 108 (1.6 g) as a white solid (1.05 g, 26%).

TLC R$_f$0.57 (EtOAc).
MS 443 (M$^+$)

Example 33

2-((4-Methoxyphenyl)sulfonylmethyl)-4-(2-pyridyl)butanoic Acid

From intermediate 94 (0.25 g), as a white solid (0.26 g, 100%).
TLC R$_f$0.22 (10% MeOH/dichloromethane).
MS 350 (MH$^+$).

Intermediate 136

2-(4-(4-Pyridinoyl)phenylsulfonylmethyl)-5-phenylpentanoic acid

From intermediate 95 (1.62 g) as white solid (1.20 g, 65).
TLC R$_f$0.65 (10% MeOH/dichloromethane).
MS

Intermediate 137

2-(4-(2-Thienoyl)phenylsulfonylmethyl)-5-phenylpentanoic Acid

From intermediate 96 (1.8 g) as a white solid (1.60 g, 80%).
TLC R$_f$0.60 (10% MeOH/dichloromethane).
MS 442 (M$^+$).

Intermediate 138

2-(4-(4-Pyridinoyl)phenylsulfonylmethyl)-5-(3,3,4-trimethylhydantoin-1-yl)pentanoic Acid From intermediate 97 (0.25 g), as a white solid (0.12 g, 50%).
TLC R$_f$0.45 (EtOAc).
MS 502 (MH$^+$).

Intermediate 139

2-(4-(2-Thienoyl)phenylsulfonylmethyl)-5-(3,3,4-trimethylhydantoin-1-yl)pentanoic Acid From intermediate 98 (1.3 g), as white solid (1.2 g, 85%).
TLC R$_f$0.45 (EtOAc).
MS 506 (M$^+$).

Intermediate 140

2-((4-Hydroxyphenyl)sulfonylmethyl)-5-phenylpentanoic Acid

From intermediate 99 (3.0 g) as white solid (3.1 g, 95%).
TLC R$_f$0.30 (EtOAc).
MS 348 (M$^+$).

Example 34

2-((Quinolin-8-yl)sulfonylmethyl)-5-phenylpentanoic Acid

From intermediate 100 (100 g) as white solid (60 mg, 55%).
TLC R$_f$0.30 (EtOAc).
MS 391 (M$^+$).

Example 35

2-(3-Phenylpropylsulfonyl)methyl-5-phenylpentanoic Acid

From intermediate 106 (1.6 g), as colourless solid (1.45 g, 90%).
TLC R$_f$0.75 (ether)
MS 374 (M$^+$).

Intermediate 141

4-Methoxy-1-(2-phenylethylsulfonyl)benzene

From intermediate 26 (8.9 g), as white solid (10.0 g, 100%).
TLC R$_f$0.75 (ether).

Example 36

3-(4-Methoxybenzenesulfonyl)-4-phenylbutanoic Acid n-Butyllithium (12.5 mmol) was added to a solution of intermediate 141 (2.75 g) in THF at −78° C. and the solution was stirred for 4 h at that temperature, then a solution of lithium bromoacetate (10 mmol) was added dropwise. The mixture was stirred at −78° C. for 2 h, then warmed to room temperature, quenched with dilute aqueous HCl and evaporated in vacuo. The residue was dissolved in dilute NaOH, washed with ether, acidified with aqueaous HCl and extracted with ethyl acetate. The ethyl acetate extracts were combined, washed with water, dried and evaporated and the residue purified by flash column chromatography, eluting with 40% EtOAc in hexane, to give the title compound as colourless solid (150 mg, 7%).
TLC R$_f$0.40 (40% EtOAc/hexanes).

Intermediate 142

2-((1-tert-Butyloxycarbonylpiperidin-4-yl)sulfonylmethyl)-5-phenylpentanoic Acid Oxone® (13 g) was added to a solution of intermediate 109 (4.5 g) and sodium acetate (5 g) in methanol 200 ml) and water (50 ml) at room temperature and the mixture was stirred for 18 h, then evaporated, diluted with water and the product collected by filtration to give the title compound as white solid (3.50 g, 75%).
TLC R$_f$0.35 (EtOAc)
MS 439 (M$^+$).

Intermediate 143

Methyl 2-((Pyrrolidin-1-yl)sulfonylmethyl)-5-phenylpentanoate

Pyrrolidine (0.2 ml) was added to a solution of intermediate 58 (0.7 g) and triethylamine (0.5 ml) in dichloromethane (20 ml) at −10° C. and the solution was stirred for 18 h, then washed with water, sodium bicarbonate and 0.5 M HCl. The solvent was dried and evaporated and the residue was purified by flash column chromatography, eluting with 40% ether/hexanes, to give the title compound as colourless oil (0.16 g, 25%).
TLC R$_f$0.28 (40% ether/hexanes).

Intermediate 144

2-((Pyrrolidin-1-yl)sulfonylmethyl)-5-phenylpentanoic Acid

Lithium hydroxide (100 mg) was added to a solution of the ester intermediate 143 (0.16 g) in methanol (5 ml) THF (10 ml) and water (5 ml) and the solution was stirred for 6 h, then evaporated in vacuo and the residue dissolved in water. The aqueous solution was washed with ether, then acidified with citric acid and extracted with dichloromethane. The dichloromethane extracts were combined and washed with water, dried and evaporated to give the crude product. This material was purified by flash column chromatography, eluting with 60% ether/hexanes, to give the title compound as colourless oil (60 mg, 40%).

TLC $R_f$ 0.40 (60% ether/hexanes).

Example 37

2-(4-Benzoylphenylsulfonylmethyl)-5-phthalimidopentanoic Acid N-Hydroxyamide

A solution of example 2 (0.1 g) in anhydrous THF (10 ml) was treated at room temperature with O-(tert-butyldimethylsilyl)hydroxylamine (0.032 g) and 1-(3-dimethylaminopropyl)-3-ethylcarbodiimide hydrochloride (0.042 g). The mixture was stirred for 24 hours and the organic solvent removed in vacuo. The residue was partitioned between water (30 ml) and ethyl acetate (50 ml). The organic extract were was washed with brine (40 ml), dried over magnesium sulfate and filtered. The filtrate was evaporated in vacuo and the residue dissolved in THF (10 ml). The solution was treated at 0° C. with a 1.0 M solution of tetrabutylammonium fluoride in THF (1.0 ml) and stirred for 1 hour. The solvent was removed in vacuo and the residue partitioned between ethyl acetate (50 ml) and water (40 ml). The organic layer was washed with brine (20 ml), dried over magnesium sulfate, filtered and the filtrate evaporated in vacuo. The residue was purified by column chromatography on silica gel eluting with 2% methanol in dichloromethane to yield the title compound as a white solid (0.06 g, 58%).

TLC $R_f$ 0.74 (ethyl acetate)
MS 521 MH$^+$

Similarly prepared were:

Example 38

3-(4-Benzoylphenylsulfonyl)propanoic Acid N-Hydroxy Amide

From intermediate 123 (0.158 g) as a white solid (0.032 g, 20%).
TLC $R_f$ 0.15 (5% methanol-dichloromethane)
MS 334 MH$^+$

Example 39

2-(4-Acetylphenylsulfonylmethyl)-5-phenylpentanoic Acid N-Hydroxy Amide

From example 3 (0.080 g) as a white solid (0.022 g, 30%).
TLC $R_f$ 0.36 (5% methanol-dichloromethane)
MS 389 MH$^+$

Example 40

2-(Thiazol-2-ylsulfonylmethyl)-5-phenylpentanoic Acid N-Hydroxy Amide

From intermediate 124 (0.125 g) as an oily semi-solid (0.023 g, 26%).
TLC $R_f$ 0.3 (5% methanol-dichloromethane)
MS 354 MH$^+$

Example 41

2-(4-(N,N-Dimethylcarbamoylphenylsulfanylmethyl)-5-phenylpentanoic Acid N-Hydroxy Amide From example 4 (0.232 g) as a white solid (0.046 g, 25%).
TLC $R_f$ 0.49 (10% methanol-dichloromethane)
MS 419 MH$^+$

Example 42

2-(4-Methoxyphenylsulfonylmethyl)-5-phthalimidopentanoic Acid N-Hydroxy Amide

From example 5 (0.35 g), as a white solid (0.12 g, 43%).
TLC $R_f$ 0.52 (5% methanol-dichloromethane)
MS 447 MH$^+$

Example 43

2-(4-Methoxyphenylsulfonylmethyl)-4-phthalimidobutanoic Acid N-Hydroxy Amide

From example 6 (0.3 g), as a white solid (0.11 g, 35%).
TLC $R_f$ 0.48 (5% methanol-dichloromethane)
MS 433 MH$^+$

Example 44

2-(4-Bromophenylsulfonyl)propanoic Acid N-Hydroxy Amide

From intermediate 125 (130 mg) as a white solid (87 mg, 64%).
TLC $R_f$ 0.1 (1:2 hexane-ethyl acetate)
MS 310 MH$^+$

Example 45

3-[4-Chlorophenyl)phenylsulfonyl]propanoic Acid N-Hydroxy Amide

From intermediate 126 (123 mg), as a white solid (39 mg, 30%).
TLC $R_f$ 0.1 (10% diethyl ether-hexane)
MS 341 MH$^+$

Example 46

3-(4-Methoxyphenylsulfonyl)propanoic Acid N-Hydroxy Amide

From intermediate 127 (764 mg), as a white solid (100 mg, 12%).
TLC $R_f$ 0.1 (1:2 hexane-ethyl acetate)
MS 227 MNH$_4^+$

Example 47

3-(4-Methoxyphenylsulfinyl)propanoic Acid N-Hydroxy Amide

From intermediate 122 (200 mg), as a colourless oil (32 mg, 15%).
TLC $R_f$ 0.1 (1:1 hexane-ethyl acetate)
MS 261 MNH$_4^+$

Example 48

2-[(4-Benzoylphenyl)sulfinylmethyl]-5-phenylpentanoic Acid N-Hydroxy Amide

From example 1 (450 mg), as a white solid (42 mg, 9%).
TLC $R_f$ 0.3 (ethyl acetate)
MS 436 MH+

Example 49

2-(Furan-2-ylmethylsulfonylmethyl)-5-phenylpentanoic Acid N-Hydroxy Amide

From example 7 (350 mg), as a colourless oil (228 mg, 62%).

TLC $R_f$ 0.4 (1:2 hexane-ethyl acetate)
MS 369 MNH$_4^+$

Example 50

2-(Cyclopentylsulfonylmethyl)-5-phenylpentanoic Acid N-Hydroxy Amide

From example 8 (342 mg), as a colourless oil (265 mg, 75%).
TLC $R_f$ 0.2 (1:2 hexane-ethyl acetate)
MS 357 MNH$_4^+$

Example 51

3-(4-Methoxyphenylsulfonylmethyl)-6-phenylhexanoic Acid N-Hydroxy Amide

From example 9 (135 mg), as a colourless oil (86 mg, 61%).
TLC $R_f$ 0.2 (1:2 hexane-ethyl acetate)
MS 392 MH$^+$

Example 52

2-(Phenylmethylsulfonylmethyl)-5-phenylpentanoic Acid N-Hydroxy Amide

From example 11 (0.559 g) as a white solid (0.500 g, 86%).
TLC $R_f$ 0.41 (ethyl acetate-hexane (2:1)).
MS 362 MH$^+$

Example 53

5-Phenyl-2-(phenylsulfonylmethyl)pentanoic Acid N-Hydroxy Amide

From example 12 (0.478 g), as a white solid (0.394 g, 79%).
TLC $R_f$ 0.51 (ethyl acetate-hexane (2:1))
MS 348 M$^+$

Example 54

2-(2-Methoxyphenylsulfonylmethyl)-5-phenylpentanoic Acid N-Hydroxy Amide

From example 13 (0.547 g), as a white solid (0.392 g, 69%).
TLC $R_f$ 0.25 (ethyl acetate-hexane (2:1))
MS 378 MH$^+$

Example 55

2-(3-Methoxyphenylsulfonylmethyl)-5-phenylpentanoic Acid N-Hydroxy Amide

From example 14 (0.636 g), as a white solid (0.460 g, 70%).
TLC $R_f$ 0.48 (ethyl acetate-hexane (2:1))
MS 378 MH$^+$

Example 56

2-(4-(4-Chlorophenyl)phenylsulfonylmethyl)-5-phenylpentanoic Acid N-Hydroxy Amide From example 24 (0.511 g), as a white solid (0.348 g, 66%).

TLC $R_f$ 0.61 (ethyl acetate-hexane (2:1))
MS 459, 461 (M−O+NH$_4^{30}$)

Example 57

2-(4-(Carbamoylmethyloxy)benzenesulfonylmethyl)-5-phenylpentanoic Acid, N-Hydroxy Amide From intermediate 128 (0.297 g), as a white solid (0.049 g, 16%).
TLC $R_f$ 0.18 (ethyl acetate)
MS 422 M−O+NH$_4^+$

Example 58

2-(4-Benzoylphenylsulfonylmethyl)-5-phenylpentanoic Acid N-Hydroxy Amide

From example 15 (7.4 g) as a colourless solid (3.80 g, 50%).
TLC $R_f$ 0.42 (10% methanol-dichloromethane)
MS 452 MH$^+$

Example 59

2-(4-Methoxyphenylsulfonylmethyl)-5-phenylpentanoic Acid N-Hydroxy Amide

From example 10 (0.425 g) as a white solid (0.185 g, 40%).
TLC $R_f$ 0.31 (ethyl acetate-hexane (2:1))
MS 378 MH$^+$

Example 60

2-(Pyrid-4-ylsulfonylmethyl)-5-phenylpentanoic Acid N-Hydroxy Amide

From example 16 (0.23 g), as a colourless solid (0.2 g, 80%).
TLC $R_f$ 0.2 (5% methanol-dichloromethane)
MS 337 MH$^+$

Example 61

2-(4-Acetylaminophenylsulfonylmethyl)-5-phenylpentanoic Acid N-Hydroxy Amide

From intermediate 129 (0.12 g), as a beige solid (0.04 g, 32%).
TLC $R_f$ 0.2 (5% methanol-dichloromethane)
MS 406 MH+

Example 62

2-(1-Methylimidazol-2-ylsulfonylmethyl)-5-phenylpentanoic Acid N-Hydroxy Amide

From intermediate 130 (0.20 g) as a white solid (0.06 g, 31%).
TLC $R_f$ 0.35 (10% methanol-dichloromethane)
MS 352 (MH+).

Example 63

2-(2-Phenylethyl)sulfonylmethyl)-5-phenylpentanoic Acid N-Hydroxy Amide

From example 17 (0.50 g) as a white powder (0.23 g, 42%).

TLC R$_f$ 0.4 (diethyl ether).
MS 376 (MH+).

Example 64

2-(2-Methylpropyl)sulfonylmethyl)-5-phenylpentanoic Acid N-Hydroxy Amide

From example 18 (1.7 g) as a white solid (0.85 g, 47%).
TLC R$_f$ 0.32 (diethyl ether).
MS 328 (MH+).

Example 65

2-(4-Methoxyphenylsulfonylmethyl-5-succinimidepentanoic Acid N-Hydroxy Amide

From example 19 (1.15 g) as a white solid (0.90 g, 74%).
TLC R$_f$ 0.35 (10% methanol-dichloromethane).
MS 398 (M+).

Example 66

2-(4-Benzoylphenyl)sulfonylmethyl-5-succinimidepentanoic Acid N-Hydroxy Amide

From example 20 (0.26 g) as a white solid (0.22 g, 79%).
TLC R$_f$ 0.45 (10% methanol-dichloromethane).
MS 471 (M+).

Example 67

2-(4-Methoxyphenylsulfonylmethyl-5-(3,3,4-trimethylhydantoin-1-yl)pentanoic Acid N-Hydroxy Amide From example 21 (0.6 g) as a white solid (0.45 g, 70%).
TLC R$_f$ 0.55 (10% methanol-dichloromethane).
MS 442 (MH+).

Example 68

2-(4-Methoxyphenylsulfonylmethyl)-4-(3,3,4-trimethylhydantoin-1-yl)butanoic Acid N-Hydroxy Amide From example 22 (0.42 g) as a white solid (0.22 g, 53%).
TLC R$_f$ 0.32 (10% methanol-dichloromethane).
MS 428 (MH+).

Example 69

2-(4-Methoxyphenylsulfonylmethyl)-3-phenylpentanoic Acid N-Hydroxy Amide

From example 23 (1.7 g) as a white solid (1.4 g, 78%).
TLC R$_f$ 0.55 (10% methanol-dichloromethane).
MS 349 (M+).

Example 70

4-(4-Methoxyphenylsulfonyl)butanoic Acid N-Hydroxy Amide

From intermediate 131 (500 mg), as a white solid (210 mg, 40%).
TLC R$_f$ 0.1 (1:2 hexane-ethyl acetate)
MS 291 MNH$_4^+$

Example 71

2-[4-Methoxyphenylsulfonylmethyl]pentanoic Acid N-Hydroxy Amide

From example 25 (500 mg), as a white solid (390 mg, 73%).
TLC R$_f$ 0.29 (5% methanol-dichloromethane)
MS 302 MH$^+$

Example 72

2-(4-Methoxyphenylsulfonylmethyl)-5-(methoxycarbonyl)pentanoic Acid N-Hydroxy Amide From example 132 (0.2 g), as a white solid (0.08 g, 38%).
TLC R$_f$ 0.45 (10% methanol in dichloromethane)
MS 360 MH$^+$

Example 73

2-(4-Methoxyphenylsulfonylmethyl)-3-methylbutanoic Acid N-Hydroxy Amide

From example 26 (2.2 g), as a white solid (0.46 g, 34%).
TLC R$_f$ 0.2 (10% methanol/dichloromethane)
MS 302 MH$^+$

Example 74

2-((Benzol[1,3]dioxole-5-yl)sulfanylmethyl)-5-phenylpentanoic Acid N-Hydroxy Amide From intermediate 133 as a tan solid (1.636 g, 70%)
TLC R$_f$ 0.36 (10% methanol/dichloromethane
MS 392 MH$^+$

Example 75

2-((4-Trifluoromethoxyphenylsulfonyl)methyl)-5-(1,5,5-trimethylhydantoin-3-yl)pentanoic Acid N-Hydroxy Amide From example 27 (0.46 g), as a white solid (0.36 g, 77%).
TLC R$_f$ 0.16 (ethyl acetate/hexane (3:1) with trace acetic acid)
MS 496 (MH$^+$)

Example 76

2-((4-Trifluoromethoxybenzensulfonylmethyl) pentanoic Acid N-Hydroxy Amide

From example 28 (2.70 g), as a white solid (2.09 g, 74%).
TLC R$_f$ 0.53 (10% methanol/dichloromethane)
MS 373 (M+NH$_4^+$)

Example 77

5-Phenyl-2-((tetrahydropyran-4-ylsulfonyl)methyl) pentanoic Acid N-Hydroxy Amide From intermediate 134 (0.60 g), as a white solid (0.40 g, 65%).
TLC R$_f$ 0.20 (ethyl acetate/hexane (5:1) with trace acetic acid)
MS 373 (M+NH$_4^+$)

Example 78

2-((Quinoline-2-yl)sulfonylmethyl)-5-phenylpentanoic Acid N-Hydroxy Amide

From example 29 (100 mg), as a pale yellow solid (0.046 g, 42%)

TLC $R_f$ 0.5 (6% MeOH/dichloromethane).
MS 396 (MH$^+$)

Example 79

2-(4-benzoylphenyl)sulfonylmethyl-4-(3,3,4-trimethylhydantoin-1-yl)butanoic Acid N-Hydroxy Amide From example 30 (0.25 g) as white solid (0.20 g, 80%).
TLC $R_f$ 0.55 (6% MeOH/dichloromethane)
MS 501 (M$^+$).

Example 80

2-((4-Benzoylphenyl)sulfonylmethyl)-5-(3,3,4-trimethylhydantoin-1-yl)pentanoic Acid N-Hydroxy Amide From example 31 (0.25 g) as white solid (0.20 g).
TLC $R_f$ 0.50 (6% MeOH/dichloromethane).
MS 515 (M$^+$).

Example 81

2-((4-Benzoylphenyl)sulfonylmethyl-3-phenylpropanoic Acid N-Hydroxy Amide

From example 32 (0.80 g), as a white solid (0.43 g, 50%).
TLC $R_f$ 0.43 (10% MeOH/dichloromethane).
MS 423 (M$^+$)

Example 82

2-((1-Benzoylpiperidine-4-yl)sulfonylmethyl)-5-phenylpentanoic Acid N-Hydroxy Amide From intermediate 135 (1.905 g) as white solid (0.85 g, 80%).
TLC $R_f$ 0.43 (7% MeOH/dichloromethane)
MS 458 (M$^+$).

Example 83

2-((1-tert-Butyloxycarbonylpiperidin-4-yl)sulfonylmethyl)-5-phenylpentanoic Acid N-Hydroxy Amide From intermediate 142 (3.5 g), as white foam (2.40 g, 66%).
TLC $R_f$ 0.7 (7% MeOH/dichloromethane).
MS 454 (M$^+$).

Example 84

2-(4-Methoxyphenyl)sulfonylmethyl)-4-(pyrid-2-yl)butanoic Acid N-Hydroxy Amide

From example 33 (0.26 g), as white solid (0.20 g, 75%).
TLC $R_f$ 0.5 (10% MeOH/dichloromethane).
MS 365 (MH$^+$).

Example 85

2-((4-Pyridinoylphenyl)sulfonylmethyl)-5-phenylpentanoic Acid N-Hydroxy Amide

From intermediate 136 (1.08 g), as white solid (0.75 g, 67%).

TLC $R_f$ 0.40 (7% MeOH/dichloromethane).
MS 453 (MH$^+$).

Example 86

2-(4-(2-Thienoyl)phenylsulfonylmethyl)-5-phenylpentanoic Acid N-Hydroxy Amide

From intermediate 137 (1.4 g) as white solid (0.85 g, 57%).
TLC $R_f$ 0.63 (10% MeOH/dichloromethane).
MS 457 (M$^+$).

Example 87

2-((4-(4-Pyridinoyl)phenyl)sulfonylmethyl)-5-(3,3,4-trimethylhydantoin-1yl)pentanoic Acid N-Hydroxy Amide From intermediate 138 (0.10 g), as white solid (0.025 g, 26%).
TLC $R_f$ 0.60 (10% MeOH/dichloromethane).
MS 517 (MH$^+$).

Example 88

2-((4-(2-Thienoyl)phenyl)sulfonylmethyl)-5-(3,3,4-trimethylhydantoin-1-yl)pentanoic Acid N-Hydroxy Amide From intermediate 139 (1.2 g), as white solid (0.66 g, 60%).
TLC $R_f$ 0.52 (7% MeOH/dichloromethane)
MS 521 (M$^+$).

Example 89

2-((4-Hydroxyphenyl)sulfonylmethyl)-5-phenylpentanoic Acid N-Hydroxy Amide

From intermediate 140 (0.35 g), as white solid (0.20 g, 60%).
TLC $R_f$ 0.40 (7% MeOH/dichloromethane).
MS 363 (M$^+$).

Example 90

2-((Pyrrolidin-1-yl)sulfonylmethyl)-5-phenylpentanoic Acid N-Hydroxy Amide

From intermediate 144 (60 mg) as a colourless solid (30 mg, 50%).
TLC $R_f$ 0.40 (7% MeOH/dichloromethane).
MS 340 (M$^+$).

Example 91

2-((Quinolin-8-yl)sulfonylmethyl)-5-phenylpentanoic Acid N-Hydroxy Amide

From example 34 (60 mg) as white solid (20 mg, 30%).
TLC $R_f$ 0.30 (5% MeOH/dichloromethane).
MS 396 (MH$^+$).

Example 92

3-(4-Methoxyphenylsulfonyl)-4-phenylpentanoic Acid N-Hydroxy Amide

From example 36 (100 mg), as white solid (60 mg, 60%).
TLC $R_f$ 0.30 (6% MeOH/dichloromethane).
MS 348 (M$^+$)

Example 93

2-(3-Phenylpropylsulfonylmethyl)-5-phenylpentanoic Acid N-Hydroxy Amide

From example 35 (1.45 g), as white solid (1.35 g, 90%).
TLC $R_f$ 0.42 (5% MeOH/dichloromethane).
MS 389 (M+).

Example 94

3-(4-Chlorophenylsulfonyl)butanoic Acid N-Hydroxy Amide

From 3-(4-chlorophenylsulfonyl)butanoic acid (2.63 g), as a colourless solid (1.00 g, 37%).
TLC $R_f$ 0.37 (5% MeOH/dichloromethane).
MS 277 (M+).

Example 95

2-(4-Methoxyphenylsulfanyl)-5-phenylpentanoic Acid N-Hydroxy Amide

From intermediate 67 (0.53 g) as a colourless solid (0.17 g, 31%)
TLC $R_f$ 0.25 (5% MeOH/dichloromethane)
MS 345 (M+)

Example 96

5-Phenyl-2-(4-(phenylmethyl)phenylsulfonylmethyl)pentanoic Acid N-Hydroxy Amide

Example 58 (0.203 g) and triethylsilane (0.42 ml) were held at reflux in trifluoroacetic acid (10 ml) for 30 h. The solvent was removed in vacuo, and the residue triturated with hexane (twice) to leave, after vacuum drying, a red solid (0.253 g). The crude red product was then purified by chromatography on silica, with 4% methanol/dichloromethane as eluent collecting fractions at $R_f$ 0.27 to give a white solid. Further column purification of the white solid with 2% methanol/dichloromethane eluent collecting at $R_f$ 0.14 provided a white solid (0.10 g). In order to remove residual traces of the starting hydroxamic acid, the residue was further purified as follows: 2,4-Dinitrophenylhydrazine (0.15 g) was suspended in methanol and treated with concentrated sulfuric acid (0.3 ml), and the warm mixture filtered. To this was added a solution of the column purified product in methanol (3 ml), and the mixture briefly warmed. Acetone (1 ml) was added and the mixture left to crystallise. The solids were then removed by filtration, and the residue obtained by concentration of the filtrate was diluted with water (20 ml) and extracted with ethyl acetate (2×30 ml). The combined organic extracts were then washed with water (2×10 ml), brine (10 ml), dried (MgSO$_4$) and evapourated in vacuo. Purification of the red oil by chromatography on silica, with 4% methanol/dichloromethane as eluent, provided the title compound as a pale orange solid (0.061 g, 31%).
TLC $R_f$ 0.29 (4% methanol/dichloromethane)
MS 439 (M–O+NH$_4^+$)

Example 97

2-(Piperidin-4-yl)sulfonylmethyl)-5-phenylpentanoic Acid N-Hydroxy Amide Trifluoroacetate Trifluoroacetic acid (20 ml) was added to a solution of the acid example 83 (2.4 g) in dichloromethane (20 ml) at room temperature and the solution was stirred for 2 h, then evaporated in vacuo and the residue azeotroped with toluene (2×50 ml). The resulting solid ws then precipitated from methanol by addition of either to give the title compound (1.54 g, 65%).
TLC $R_f$ 0.25 (10% MeOH/dichloromethane 2% NH$_4$OH).
MS 323 (MH+).

Example 98

2-((1-Benzylpiperidin-4-yl)sulfonylmethyl)-5-phenylpentanoic Acid N-Hydroxy Amide Sodium triacetoxyborohydride (0.22 g) was added to a solution of example 97 (0.23 g), triethylamine (60 mg) and benzaldehyde (106 mg) in a mixture of dichloromethane (10 ml) and methanol (2 ml). The mixture was stirred at room temperature for 6 h, then evaporated in vacuo and the residue partitioned between water and dichloromethane. The organic solvent was washed with water, dried and evaporated and the residue purified by chromatography, eluting with 6% MeOH in dichloromethane and 1% NH$_4$OH, to give the title compound as white solid (60 mg, 25%).
TLC $R_f$ 0.35 (6% MeOH/dichloromethane 1% NH$_4$OH).
MS 445 (MH+).
Similarly prepared was:

Example 99

2-((1-(4-Cyanobenzyl)piperidin-4-yl)sulfonylmethyl)-5-phenylpentanoic Acid N-Hydroxy Amide From example 97 (0.23 g) and 4-cyanobenzaldehyde (65 mg) as white solid (35 mg, 14%).
TLC $R_f$ 0.40 (6% MeOH/dichloromethane).
MS 470 (MH+).

Intermediate 145

2-((4-Hydroxyphenyl)sulfonylmethyl)-5-phenylpentanoic Acid N-tert-Butyloxy Amide EDC (2.0 g) was added to a solution of intermediate 140 (3.5 g), triethylamine (1.0 g) and O-tert-butylhydroxylamine hydrochloride (1.3 g) in dichloromethane (100 ml) at room temperature and the mixture was stirred for 18 h. The mixture was then washed with water, 1M HCl and saturated sodium bicarbonate, dried and evaporated to give the title compound as colourless solid (4.0 g, 95%).
TLC $R_f$ 0.46 (ether)

Intermediate 146

2-((4-Benzyloxyphenyl)sulfonylmethyl)-5-phenylpentanoic Acid N-tert-Butyloxy Amide Benzyl bromide (0.16 g) was added to a suspension of intermediate 145 (0.42 g) and caesium carbonate (0.33 g) in DMF (10 ml) and the mixture was stirred for 18 h at room temperature, then added to water and extracted with ether. The solvent was washed with water and brine, dried and evaporated. The residue was purified by flash column chromatography, eluting with ether, to give the title compound as colourless oil (0.25 g, 50%).
TLC $R_f$ 0.70 (ether).
Similarly prepared were

Intermediate 147

2-(4-(1-Methyleth-1-yloxy)phenylsulfonylmethyl)-5-phenylpentanoic Acid N-tert-Butyloxy Amide From intermediate 145 (0.42 g), as colourless oil (0.35 g, 80%).
TCL $R_f$ 0.65 (ether).

Intermediate 148

2-((4-Butyloxy)phenylsulfonylmethyl)-5-phenylpentanoic Acid N-tert-Butyloxy Amide From intermediate 145 (0.42 g), as colourless oil (0.40 g, 90%).

TLC $R_f$ 0.75 (ether).

Intermediate 149

2-((4-Cyclopentyloxy)phenylsulfonylmethyl)-5-phenylpentanoic Acid N-tert-Butyloxy Amide From intermediate 145 (0.42 g), as colourless oil (0.40 g, 90%).

TLC $R_f$ 0.68 (ether).

Intermediate 150

2-(4-(4-Cyanobenzyloxy)phenylsulfonylmethyl)-5-phenylpentanoic Acid N-tert-Butyloxy Amide From intermediate 145 (0.42 g) as colourless oil (0.35 g, 75%).

TLC $R_f$ 0.63 (ether).

Example 100

2-((4-Benzyloxyphenyl)sulfonylmethyl)-5-phenylpentanoic Acid N-hydroxy Amide

A solution of intermediate 146 (0.17 g) in TFA (10 ml) and dichloromethane (10 ml) was stirred overnight and then evaporated in vacuo. The residue was azeotroped with toluene, then purified by flash column chromatography, eluting with 7% MeOH/dichloromethane, to give the title compound as colourless solid (0.06 g, 40%).

TLC $R_f$ 0.45 (5%MeOH/dichloromethane).

MS 453 (M$^+$).

Example 101

2-(4-(1-Methyleth-1-yloxy)phenylsulfonylmethyl)-5-phenylpentanoic Acid N-Hydroxy Amide From intermediate 147 (0.35 g) as white solid (0.20 g, 48%).

TLC $R_f$ 0.25 (5% MeOH/dichloromethane).

MS 405 (M').

Example 102

2-((4-Butyloxy)phenylsulfonylmethyl)-5-phenylpentanoic Acid N-Hydroxy Amide

From intermediate 148 (0.40 g) as white solid (0.20 g, 45%).

TLC $R_f$ 0.30 (5% MeOH/dichloromethane).

MS 419 (M$^+$).

Example 103

2-((4-Cyclopentyloxyphenyl)sulfonylmethyl)-5-phenylpentanoic Acid N-Hydroxy Amide From intermediate 149 (0.40 g), as white solid (0.15 g, 33%).

TLC $R_f$ 0.30 (5% MeOH/dichloromethane).

MS 431 (M$^+$).

Example 104

2-(4-(4-Cyanobenzyloxy)phenylsulfonylmethyl)-5-phenylpentanoic Acid N-Hydroxy Amide From intermediate 150 (0.25 g) as white solid (0.265 g, 100%).

TLC $R_f$ 0.25 (6% MeOH/dichloromethane).

MS 469 (M$^+$).

Example 105

2-((4-(1-Hydroxy-1-phenylmethyl)phenyl)sulfonylmethyl)-5-phenylpentanoic Acid N-Hydroxy Amide Sodium borohydride (0.38 g) was added to a solution of example 58 (0.45 g) in MeOH (100 ml) and the solution was stirred for 2 h, then evaporated and the residue dissolved in water, acidified with citric acid and extracted with ethyl acetate. The organic layer was washed with brine, dried and evaporated to give the crude product, which was purified by column chromatography, eluting with 7% MeOH in dichloromethane to give the title compound (0.43 g, 95%) as white solid.

TLC $R_f$ 0.53 (7% MeOH/dichloromethane).

MS 454 (M$^+$).

Example 106

2-(Pyrid-4-ylsulfonylmethyl)-5-phenylpentananoic Acid N-Hydroxy Amide Hydrochloride Example 60 was dissolved in dichloromethane and treated with excess 1M HCl in diethyl ether and then evaporated to give the title compound (0.20 g) as a pale yellow solid.

Example 107

4-[4-(Methyoxycarbonyl)methoxy-3,5-dimethyphenyl]-2-methyl-1(2H)phthalazinone

Intermediate 60 (1.40 g) was added to a suspension of sodium hydride (0.24 g) in DMF (30 ml) at 0° C. After stirring for 30 min, methyl bromoacetate (1.15 g) was added and the mixture stirred for 18 h. Water (90 ml) was added and the resultant precipitate was collected by filtration and dried in vacuo to provide the title compound as a white solid (1.54 g)

MS 353 MH$^+$

Example 108

4-[4-(Carboxy)methoxy-3,5-dimethyphenyl]-2-methyl-1(2H)phthalazinone

Lithium hydroxide monohydrate (0.22 g) was added to a solution of example 107 (1.52 g) in aqueous tetrahydrofuran (1:1 50 ml) and the reaction stirred 18 h, the mixture was the concentrated in vacuo and the residual slurry acidified with 10% hydrochloric acid. The resulting precipitate was collected to give the title compound as a white solid (1.36 g).

MS 338 MH$^+$

Example 109

4-[4-(Hydroxyaminocarbonyl)methoxy-3,5-dimethyphenyl]-2-methyl-1(2H)phthalazinone A solution of example 108 (1.15 g) in dichloromethane (30 ml) at 0° C. was treated with triethylamine (0.52 g)

followed by isopropenyl chloroformate (0.41 g), and the mixture was stirred for 1 h. O-tert-butyldimethylsilylhydroxylamine (0.50 g) was then added and the mixture was stirred for a further 18 h. The reaction mixture was washed with 10% citric acid (20 ml), saturated sodium bicarbonate (20 ml) and the concentrated to dryness in vacuo. A solution of the residual solid in tetrahydrofuran (30 ml) and water (5 ml) was then treated with a 1.0 M solution of tetrabutylammonium fluoride in tetahydrofuran (1 ml) and stirred 1 h the resultant crude mixture was concentrated on to silica and purified by chromatography, eluting with 5% methanol in dichloromethane, to provide the title compound as a white solid (0.10 g).

$R_f$ 0.18 (5% methanol in dichloromethane)

Example A
Collagenase inhibition activity

The potency of compounds of general formula (I) to act as inhibitors of collagenase was determined by the procedure of Cawston and Barrett, (Anal. Biochem., 99:340–345, 1979) whereby a 1 mM solution of the inhibitor being tested or dilutions thereof was incubated at 37° C. for 16 hours with collagen and collagenase (buffered with 50 mM Tris, pH 7.6 containing 5 mM $CaCl_2$, 0.05% Brij 35, 60 mM NaCl and 0.02% $NaN_3$). The collagen was acetylated $^3H$ or $^{14}C$-collagen prepared by the method of Cawston and Murphy (Methods in Enzymolgy, 80:711, 1981). The choice of radiolabel did not alter the ability of collagenase to degrade the collagen substrate. The samples were centrifuged to sediment undigested collagen and an aliquot of the radioactive supernatant removed for assay on a scintillation counter as a measure of hydrolysis. The collagenase activity in the presence of 1 mM inhibitor, or a dilution thereof, was compared to activity in a control devoid of inhibitor and the results reported as that inhibitor concentration effecting 50% inhibition of the collagenase ($IC_{50}$).

Example B
Stomelysin inhibition activity

The potency of compounds of general formula (I) to act as inhibitors of stromelysin was determined using the procedure of Nagase et al (Methods in Enzymology Vol 254, 1994), whereby a 0.1 mM solution of the inhibitor being tested or dilutions thereof was incubated at 37° C. for 16 hours with stromelysin and $^3H$ transferrin (buffered with 50 mM Tris, pH 7.6 containing 10 mM $CaCl_2$, 150M NaCl, 0.05% Brij, 35, and 0.02% $NaN_3$). The transferrin was carboxymethylated with $^3H$ iodoacetic acid. The stromelysin activity in the presence of 1 mM, or a dilution thereof, was compared to activity in a control devoid of inhibitor and the results reported as that inhibitor concentration effecting 50% inhibition of the stromelysin ($IC_{50}$)

Example C
Gelatinase inhibition activity

The potency of the compounds of general formula (I) to act as inhibitors of gelatinase was determined using the procedure of Harris & Krane (Biochem Biophys. Acta, 258:566–576, 1972), whereby a 1 mM solution of the inhibitor being tested or dilutions thereof was incubated at 37° C. for 16 hours with gelatinase and heat denatured $^3H$ or $^{14}C$-acetylated collagen (buffered with 50mM Tris, pH 7.6 containing 5 mM $CaCl_2$, 0.05% Brij 35 and 0.02% $NaN_3$). the $^3H$ or $^{14}C$ gelatin was prepared by denaturing $^3H$ or $^{14}C$-collagen produced according to the method of Cawston and Murphy (Methods in Enzymology, 80:711, 1981) by incubation at 60° C. for 30 minutes. Undigested gelatin was precipitated by addition of trichloroacetic acid and centrifugation. The gelatinase activity in the presence of 1 mM, or dilution thereof, was compared to the activity in a control devoid of inhibitor and results reported as that inhibitor concentration effecting 50% inhibition of the gelatinase ($IC_{50}$).

Example D
MMP Inhibition Activity-Fluorimetric Assay

The potency of compounds of general formula (I) to act as inhibitors of collagenase-1(MMP-1), collagenase-2 (MMP-8), collagenase-3(MMP-13), gelatinase-A (MMP-2), gelatinase-B (MMP-9) and stromelysin-1(MMP-3) was determined using the following procedure:

Inhibitors are dissolved in dimethylsulphoxide containing 0.02% β-mercaptoethanol and serial dilutions are prepared. Activated enzyme is incubated in assay buffer containing 50 mM Tris, pH 7.4, 5 mM $CaCl_2$, 0.002% $NaN_3$ and Brij 35 in the presence and absence of inhibitor. Samples are pre-incubated at 37° C. for 15 minutes before the addition of the fluorimetric substrate (Mca-Pro-Leu-Gly-Leu-Dpa-Ala-Arg-$NH_2$) to a final concentration of 10 μM. The assay is incubated for 20–30 min at 37° C. and then read in a Fluoroscan II at $\lambda_{nx}$ (340 nm) and $\lambda_{es1}$ (405 nm).

The enzyme activity was compared to activity in a control devoid of inhibitor and the results reported as that inhibitor concentration effecting 50% inhibition of the stromelysin ($IC_{50}$).

Example E
Inhibition of TNFα production

The potency of the compounds of general formula (I) to act as inhibitors of the production of TNFα is determined using the following procedure. A 100 μM solution of the inhibitor being tested or dilutions thereof is incubated at 37° C. in an atmosphere of 5% $CO_2$ with THP-1 cells (human monocytes) suspended in RPMl 1640 medium and 20 μM β-mercaptoethanol at a cell density of $1 \times 10^6$/ml and stimulated with LPS. After 18 hours the supernatant is assayed for the levels of TNFα using a commercially available ELISA kit (R & D Systems).

The activity in the presence of 0.1 mM inhibitor or dilutions thereof is compared to activity in a control devoid of inhibitor and results reported as that inhibitor concentration effecting 50% inhibition of the production of TNFα.

Example F
Inhibition of L-selectin shedding

Compounds of general formula (I) are evaluated in an assay of L-selectin shedding by peripheral blood mononuclear cells (PBMC). PBMC are isolated from buffy coats by standard procedures using Ficoll. A 100 μM solution of the inhibitor being tested or dilutions thereof is incubated for 20 min at 37° C. in an atmosphere of 5% $CO_2$ with $4 \times 10^6$/ml PBMC stimulated with PMA. The cells are centrifuged down and the supernatants tested for sL-selectin using a commercially available ELISA kit (R & D Systems).

The activity in the presence of 100 μM inhibitor or dilutions thereof was compared to activity in a control devoid of inhibitor and results reported as that inhibitor concentration effecting 50% inhibition of the shedding of L-selectin.

Example G
Inhibition of sIl-1RII shedding

Compounds of general formula (I) are evaluated in an assay of sIl-1RII shedding by peripheral blood mononuclear cells (PBMC). PBMC are isolated from buffy coats by standard procedures using Ficoll. A 100 μM solution of the inhibitor being tested or dilutions thereof are incubated for 18 h at 37° C. in an atmosphere of 5% $CO_2$ with $2\times10^6$/ml PBMC stimulated with Il-13. The cells are centrifuged down and the supernatants tested for sIl-1RII using a commercially available ELISA kit (R & D Systems).

The activity in the presence of 100 µM inhibitor or dilutions thereof is compared to activity in a control devoid of inhibitor and results reported as that inhibitor concentration effecting 50% inhibition of the shedding of sIl-1RII.

Example H
Inhibition of Il-6R shedding

Compounds of general formula (I) are evaluated in an assay of sIl-6R shedding by HL-60 cells. PBMC are isolated from buffy coats by standard procedures using Ficoll. A 100 µM solution of the inhibitor being tested or dilutions thereof is incubated for 24 h at 37° C. in an atmosphere of 5% $CO_2$ with $2\times10^6$/ml HL-60 cells stimulated with PMA. The cells are centrifuged down and the supernatants tested for sIl-6R using a commercially available ELISA kit (R & D Systems).

The activity in the presence of 100 µM inhibitor or dilutions thereof is compared to activity in a control devoid of inhibitor and results reported as that inhibitor concentration effecting 50% inhibition of the shedding of Il-6R.

Example I
Inhibition of TNF RII shedding

The potency of the compounds of general formula (I) to act as inhibitors of the shedding of TNF RII is determined using the following procedure. A 100 µM solution of the inhibitor being tested or dilutions thereof are incubated at 37° C. in an atmosphere of 5% $CO_2$ with THP-1 cells (human monocytes) suspended in RPMl 1640 medium and 20 µM β-mercaptoethanol at a cell density of $1\times10^6$/ml and stimulated with LPS. After 18 hours the supernatant is assayed for the levels of sTNF RII using a commercially available ELISA kit (R & D Systems).

The activity in the presence of 0.1 mM inhibitor or dilutions thereof is compared to activity in a control devoid of inhibitor and results reported as that inhibitor concentration effecting 50% inhibition of the shedding of TNF RII.

Example J
Adjuvant arthritic rat model

Compounds of general formula (I) were evaluated in an adjuvant arthritis model in the rat based on the methods employed by B. B. Newbould (1963), Br. J. Pharmacol, 21, 127–136 and C. M. Pearson and F. D. Wood (1959), Arthritis Rheum, 2, 440–459. Briefly male Wistar rats (180–200 g) were injected at the base of the tail with Freund's adjuvant. Twelve days later the responding animals were randomised into experimental groups. Compounds of general formula (I) were dosed either orally as a suspension in 1% methyl cellulose or intraperitoneally in 0.2% carboxymethylcellulose from day 12 to the end of the experiment on day 22. Hind paw volumes were measured every two days from day 12 onwards and X-rays were taken of the hind feet on completion of the experiment. Results were expressed as the percent increase of foot volume over ay 12 values.

Example K
Mouse ovarian carcinoma xenograft model

Compounds of general formula (I) were evaluated in an ovarian carcinoma xenograft model of cancer, based on that described by B. Davies et al (1993), Cancer Research, 53, 2087–2091 This model, in brief, consists of inoculating female nu/nu mice with $1\times10^9$ OCVAR3-icr cells into the peritoneal cavity. Compounds of general formula (I) are administered by the oral route as a suspension in 1% methyl cellulose or intraperitoneally as a suspension in phosphate buffered saline in 0.01% Tween-20. At the conclusion of the experiment (4–5 weeks) the number of peritoneal cells are counted and any solid tumour deposits weighed. In some experiments tumour development is monitored by measurement of tumour specific antigens.

Example L
Rat mammary carcinoma model

Compounds of general formula (I) were evaluated in a HOSP.1 rat mammary carcinoma model of cancer (S. Eccles et al (1995), Cancer Research, in press). This model consists of the intravenous inoculation of female CBH/cbi rats with $2\times10^4$ tumour cells into the jugular vein. Compounds of general formula (I) are administered by the oral route as a suspension in 1% methyl cellulose or intraperitoneally as a suspension in phosphate buffered saline+0.01% Tween-20. At the conclusion of the experiment (4–5 weeks) the animals are killed, the lungs are removed and individual tumours counted after 20 hours fixation in Methacam.

Example M
Mouse B16 melanoma model

The anti-metastatic potential of compounds of general formula (I) is evaluated in a B16 melanoma model in C57BL/6. Mice are injected intravenously with $2\times10^5$ B16F10 murine tumour cells harvested from in vitro cultures. Inhibitors are administered by the oral route as a suspension in 1% methyl cellulose or intraperitoneally as a suspension in phosphate buffered saline pH7.2+0.01% Tween-20. Mice are killed 14 days after cell inoculation and the lungs removed and weighed prior to fixing in Bouin's solution. The number of colonies present on the surface of each set of lungs is then counted by eye.

What is claimed is:

1. A compound of formula (I)

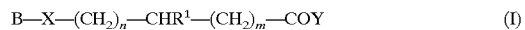

$$B-X-(CH_2)_n-CHR^1-(CH_2)_m-COY \qquad (I)$$

wherein m and n are each independently 0 or 1, but are not both 0;

X is $S(O)_{0-2}$;

Y is selected from the group consisting of $OR^2$ and NHOH;

$R^1$ is H or is a group selected from the group consisting of H, $C_{1-6}$ alkyl, $C_{2-6}$ alkenyl, aryl, $C_{1-6}$ alkyl-aryl, heteroaryl, $C_{1-6}$ alkyl-heteroaryl, heterocycloalkyl, $C_{1-6}$ alkyl-heterocycloalkyl, cycloalkyl, and $C_{1-6}$ alkyl-cycloalkyl, and said group is optionally substituted with $R^9$;

$R^2$ is selected from the group consisting of h and $C_{1-6}$ alkyl;

B is selected from the group consisting of heterocycloalkenyl and heterocycloalkyl optionally substituted by a substituent selected from the group consisting of $R^5$, $C_{1-6}$ alkyl-$R^5$, $C_{3-6}$ alkenyl-$R^7$, aryl optionally substituted with $R^5$, aryl-$C_{1-6}$ alkyl-$R^5$, $C_{1-6}$ alkyl-aryl optionally substituted with $R^5$, $C_{1-6}$ alkyl-heteroaryl optionally substituted with $R^5$, aryl-$C_{2-6}$ alkenyl-$R^5$, heteroaryl optionally substituted with $R^5$, heteroaryl-$C_{1-6}$ alkyl-$R^5$, cycloalkyl optionally substituted with $R^5$, benzofused cycloalkyl optionally substituted with $R^5$, heterocycloalkyl optionally substituted with $R^5$, benzofused heterocycloalkyl optionally substituted with $R^5$, and the groups:

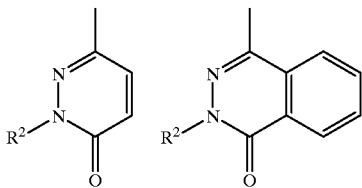
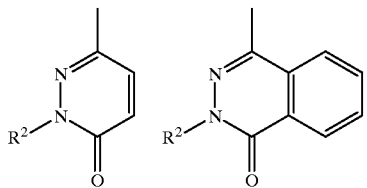

$R^5$ is selected from the group consisting of $C_{1-6}$ alkyl, $C_{2-6}$ alkenyl-$R^7$, halogen, CN, $NO_2$, $N(R^6)_2$, $OR^6$, $COR^6$, $CO_2R^2$, $CON(R^6)_2$, $NR^6R^7$, $S(O)_{0-2}R^8$, and $SO_2N(R^6)_2$;

$R^6$ is H or a group selected from the group consisting of $C_{1-6}$ alkyl, aryl, $C_{1-6}$ alkyl-aryl, heteraryl, $C_{1-6}$ alkyl-heteroaryl, cycloalkyl, $C_{1-6}$ alkyl-cycloalkyl, heterocycloalkyl, and $C_{1-6}$ alkyl-heterocycloaklyl, wherein said group is optionally substituted with a substituent selected from the group consisting of $R^8$, $COR^8$, $SO_{0-2}R^8$, $CO_2R^8$, $OR^8$, $CONR^2R^8$, $NR^2R^8$, halogen, CN, $SO_2NR^3R^8$, and $NO_2$, and for each case of $N(R^6)_2$ the $R^6$ groups are the same or different or $N(R^6)_2$ is heterocycloalkyl optionally substituted with a substituent selected from the group consisting of $R^8$, $COR^8$, $SO_{0-3}R^8$, $OR^8$, $CONR^2R^8$, $NR^2R^8$, halogen, CN, $SO_2NR^2R^8$, and $NO_2$;

$R^7$ is selected from the group consisting of $COR^6$, $CON(R^6)_2$, $CO_2R^8$, and $SO_2R^8$;

$R^8$ is selected from the group consisting of $C_{1-6}$ alkyl, aryl, $C_{1-6}$ alkyl-aryl, heteroaryl, and $C_{1-6}$ alkyl-heteroaryl; and $R^9$ is selected from the group consisting of $OR^6$, $COR^6$, $CO_2R^3$, $CON(R^6)_2$, $NR^6R^7$, $S(O)_{0-2}R^8$, $SO_2N(R^6)_2$, phthalimido, succinimido, and the group

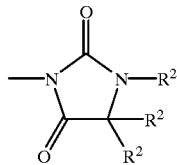

or a salt, solvate, hydrate, or protected amino or protected carboxy derivative thereof.

2. The compound, according to claim 1, wherein

R' is H or selected from the group consisting of optionally-substituted alkyl, alkenyl, aryl, alkyl-aryl, heteroaryl, and alkyl-heteroaryl;

B is heterocycloalkyl optionally substituted by a substituent selected from the group consisting of $R^5$, $C_{1-6}$ alkyl-$R^5$, $C_{2-6}$ alkenyl-$R^5$, aryl optionally substituted with $R^5$, aryl-$C_{1-6}$ alkyl-$R^3$, aryl $C_{3-6}$ alkenyl-$R^7$, heteroaryl optionally substituted with $R^5$, cycloalkyl optionally substituted with $R^5$, benzofused $C_{5-6}$ cycloalkyl optionally substituted with $r^5$, heterocycloalkyl optionally substituted with $R^5$, benzofused $C_{5-6}$ heterocycloalkyl optionally substituted with $R^5$, and the groups:

$R^5$ is selected from the group consisting of $C_{1-6}$ alkyl, $C_{2-6}$ alkenyl-$R^5$, halogen, CN, $NO_2$, $N(R^6)_2$, $OR^6$, $OC_{1-4}$ alkyl-$R^7$, $COR^6$, $CO_2R^2$, $CON(R^6)_2$, $NR^6R^7$, $S(O)_{0-2}R^5$, and $SO_2N(R^6)_2$; and $R^6$ is selected from the group consisting of H, alkyl, aryl, alkyl-aryl, heteroaryl, and alkyl-heteroaryl.

3. The compound, according to claim 1, wherein $R^1$ is H or a group optionally substituted with $R^9$ selected from the group consisting of $C_{1-6}$ alkyl, $C_{2-6}$ alkenyl, $C_{1-6}$ alkyl-aryl, $C_{1-6}$ alkyl-heteroaryl, $C_{1-6}$ alkyl-heterocycloalkyl, and $C_{1-6}$ alkyl-cycloalkyl.

4. The compound, according to claim 1, wherein $R^5$ is selected from the group consisting of halogen, CN, $NO_2$, $N(R^6)_2$, $OR^6$, $COR^6$, $CON(R^6)_2$, $NR^6R^7$, and $S(O)_{0-2}R^8$.

5. The compound, according to claim 1, wherein $R^7$ is $COR^6$.

6. The compound, according to claim 1, wherein $R^9$ is selected from the group consisting of $OR^6$, $CP_2R^2$, $CON(R^6)_2$, phthalimido, and succinimido.

7. The compound, according to claim 1, in the form of a single enantiomer or diastereomer.

8. A pharmaceutical composition, comprising a compound of claim 1, and a pharmaceutically-acceptable diluent or carrier.

9. A method for the treatment of a condition associated with matrix metalloproteinasesor that is mediated by TNFα or enzymes involved in the shedding of L-selectin, the TNF receptors or IL-6 receptors, wherein said method comprises the administration of an effective amount of a compound of claim 1.

10. The method, according to claim 9, wherein said condition is selected from the group consisting of cancer, inflammation and inflammatory diseases, tissue degeneration, periodontal disease, ophthalmological disease, dermatological disorders, fever, cardiovascular effects, haemorrhage, coagulation and acute phase response, cachexia, anorexia, acute infection, HIV infection, shock states, graft versus host reactions, autoimmune disease, reperfusion injury, meningitis and migraine.

11. The method, according to claim 9, wherein said condition is selected from the group consisting of tumor growth, angiogenesis, tumor invasion and spread, metastases, malignant ascites, and malignant pleural effusion.

12. The method, according to claim 9, wherein said condition is selected from the group consisting of cerebral ischaemia, ischaemic heart disease, rheumatoid arthritis, osteoarthritis, osteoporosis, asthma, multiple sclerosis, neurodegeneration, Alzheimer's, atherosclerosis, stroke, vasculitis, Crohn's disease and ulcerative colitis.

13. The method, according to claim 9, wherein said condition is selected from the group consisting of corneal ulceration, retinopathy, and surgical wound healing.

14. The method, according to claim 9, wherein said condition is selected from the group consisting of psoriasis, atopic dermatitis, chronic ulcers, and epidermolysis bullosa.

15. The method, according to claim 9, wherein said condition is selected from the group consisting of periodontitis, and gingivitis.

16. The method, according to claim 9, wherein said condition is selected from the group consisting of rhinitis, allergic conjunctivitis, eczema, and anaphylaxis.

17. The method, according to claim 9, wherein said condition is selected from the group consisting of restenosis, congestive heart failure, endometriosis, atherosclerosis, and endosclerosis.

* * * * *

UNITED STATES PATENT AND TRADEMARK OFFICE
CERTIFICATE OF CORRECTION

PATENT NO. : 6,118,001
DATED : September 12, 2000
INVENTOR(S) : Owen et al.

It is certified that error appears in the above-identified patent and that said Letters Patent is hereby corrected as shown below:

Column 54,
Line 48 "of H, $C_{1-6}$" should read -- of $C_{1-6}$ --.
Line 53, "consisting of h and" should read -- consisting of H and --.
Line 58, "$C_{3-6}$ alkenyl-$R^7$," should read -- $C_{2-6}$ alkenyl-$R^7$, --.

Column 55,
Line 17, "heteraryl, $C_{1-6}$" should read -- heteroaryl, $C_{1-6}$ --.
Line 24, "$SO_2NR_3R_8$," should read -- $SO_2NR^2R^8$, --.
Line 29, "$SO_{0-3}R8$," should read -- $SO_{0-2}R^8$, --.
Line 37, "$CO_2R^3$," should read -- $CO_2R^2$, --.
Line 60, "aryl-$C_{1-6}$ alkyl-$R^3$," should read -- aryl-$C_{1-6}$ alkyl-$R^5$, --.
Line 63, "with $r^5$," should read -- with $R^5$, --.

Column 56,
Lines 13-14, "$S(O)_{0-2}R^5$," should read -- $S(O)_{0-2}R^8$, --.
Line 30, "$CP_2R^2$," should read -- $CO_2R^2$, --.

Signed and Sealed this

Twenty-fifth Day of June, 2002

Attest:

*Attesting Officer*

JAMES E. ROGAN
*Director of the United States Patent and Trademark Office*